United States Patent
Bastian et al.

(10) Patent No.: US 9,872,853 B2
(45) Date of Patent: Jan. 23, 2018

(54) 2,3-DIHYDRO-1H-INDOLE COMPOUNDS

(71) Applicant: Eli Lilly and Company, Indianapolis, IN (US)

(72) Inventors: Jolie Anne Bastian, Indianapolis, IN (US); Jiehao Chen, Carmel, IN (US); Jeffrey Daniel Cohen, Indianapolis, IN (US); James Robert Henry, Indianapolis, IN (US); William Thomas McMillen, Indianapolis, IN (US); Bradley Earl Reaman, Indianapolis, IN (US); Almudena Rubio, Carmel, IN (US); Daniel Jon Sall, Greenwood, IN (US); Gaiying Zhao, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/609,115

(22) Filed: May 31, 2017

(65) Prior Publication Data

US 2017/0354641 A1 Dec. 14, 2017

Related U.S. Application Data

(60) Provisional application No. 62/348,457, filed on Jun. 10, 2016.

(51) Int. Cl.
| | |
|---|---|
| *A61K 31/403* | (2006.01) |
| *C07D 209/12* | (2006.01) |
| *C07D 209/02* | (2006.01) |
| *C07C 233/57* | (2006.01) |
| *C07C 233/01* | (2006.01) |
| *C07D 309/00* | (2006.01) |

(52) U.S. Cl.
CPC .......... *A61K 31/403* (2013.01); *C07C 233/57* (2013.01); *C07D 209/02* (2013.01); *C07C 233/01* (2013.01); *C07D 309/00* (2013.01)

(58) Field of Classification Search
CPC ........................... C07D 209/12; A61K 31/403
See application file for complete search history.

(56) References Cited

U.S. PATENT DOCUMENTS

2009/0270408 A1  10/2009  Mortell et al.

FOREIGN PATENT DOCUMENTS

| WO | 2010/005958 A2 | 1/2010 |
| WO | 2012/142237 A1 | 10/2012 |
| WO | 2014/150646 A1 | 9/2014 |

OTHER PUBLICATIONS

CAS 1359420-19-1, CAS 1359035-89-4, CAS 1359002-77-9, CAS 1358912-57-8, CAS 1358648-68-6, CAS 1357815-05-4, American Chemical Society (2017)
Lin, Shu-Yu, Phenyl Benzenesulfonylhydrazides Exhibit Selective Indoleamine 2,3-Dioxygenase Inhibition with Potent in Vivo Pharmacodynamic Activity and Antitumor Efficacy, Journal of Medicinal Chemistry (2016), vol. 59, pp. 419-430.
Dounay et al., "Challenges and opportunities in the Discovery of New therapeutics Targeting the Kynurenine Pathway", Journal of Medicinal Chemistry (2015), vol. 58 No. 22, pp. 8762-8782.
Röhrig et al., "Challenges in the Discovery of Indoleamine 2, 3-Dioxygenase 1 (ID01) Inhibitors", Journal of Medicinal Chemistry (2015), vol. 58 No. 24, pp. 9421-9437.

*Primary Examiner* — Rebecca L Anderson
*Assistant Examiner* — Karen Cheng
(74) *Attorney, Agent, or Firm* — John C. Demeter; Tina M. Tucker

(57) ABSTRACT

The present invention relates to certain novel 2,3-dihydro-1H-indole compounds, pharmaceutical compositions comprising the compounds, and methods of using the compounds to treat cancer, more particularly for the treatment of cancer selected from the group consisting of melanoma, acute myeloid leukemia, chronic lymphocytic leukemia, colorectal cancer, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma.

8 Claims, No Drawings

2,3-DIHYDRO-1H-INDOLE COMPOUNDS

The present invention relates to novel 2,3-dihydro-1H-indole compounds that inhibit the conversion of tryptophan to kynurenine, certain of which have been confirmed to bind to indoleamine 2,3-dioxygenase (IDO1). The present invention also relates to pharmaceutical compositions comprising these compounds and methods of using these compounds to treat physiological disorders, more particularly for the treatment of cancer such as melanoma, acute myeloid leukemia, chronic lymphocytic leukemia, colorectal cancer, renal cell carcinoma, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma.

Tryptophan is an essential amino acid required for protein biosynthesis, cellular growth, the generation of neuroactive metabolites such as serotonin (5-hydroxytryptamine), melatonin, and the co-enzyme nicotinamide adenine dinucleotide (NAD). Tryptophan is catabolized by indoleamine 2,3-dioxygenase (IDO1), a heme-dependent enzyme that catalyzes the first and rate-limiting step in tryptophan catabolism to N-formyl-kynurenine, which is then deformylated to generate kynurenine. During infection, the expression of IDO1 is induced by interferon gamma to locally deplete tryptophan, which inhibits the growth of tryptophan-dependent intracellular pathogens such as *Chlamydia trachomatis, Toxoplasma gondii*, and viruses. Additionally, IDO1 plays a role in preventing oxidative damage in cells, several neuro-pathologies, regulation of the immune system, and cancer. Although IDO1 activity is a critical component of the immune response to pathogens, prolonged activity results in the depletion of extracellular tryptophan with the concomitant production of kynurenine, both of which are immunosuppressive. IDO1 expression in cancer is well documented and occurs through both intrinsic activation of IDO1 gene expression and/or through the activation of the IFN-γ-to-IDO1 axis, a result of immune cell activation. Additionally, innate immune cells such as dendritic cells, monocytes and macrophages, which are recruited to sites of inflammation and the tumor microenvironment, are immunosuppressive when they express IDO1. Together the IDO1-dependent depletion of tryptophan and production of kynurenine have been linked to suppression of T-cell activation and proliferation and NK cell function. Furthermore depletion of tryptophan and production of kynurenine are critical for the formation of regulatory T cells (Treg) and myeloid-derived suppressor cells (MDSCs), which function to dampen immune cell activation. These IDO1 dependent immunosuppressive mechanisms are components that allow tumors to circumvent the immune system.

Potential inhibitors of kynurenine production through IDO1 inhibition are already known in the literature. See for example, WO2010005958, WO2012142237 and WO2014150646 and Journal of Medicinal Chemistry (2016), 59(1), 419-430. Certain 2,3-dihydro-1H-indole compounds are known in the art. See for example, CAS registry numbers 1359420-19-1, 1358912-57-8, 1358648-68-6, 1357815-05-4, 1359035-89-4, and 1359002-77-9.

There is a need for new cancer treatments. In particular there is a need for new cancer treatments for melanoma, acute myeloid leukemia, chronic lymphocytic leukemia, colorectal cancer, renal cell carcinoma, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma. There remains a need to provide alternative kynurenine production inhibitors useful in the treatment of cancer. Preferably such compounds have properties that enable optimal dosing required for maximal inhibition of tumor cell growth while having acceptable tolerability for the patient. Preferably such compounds would also be orally bioavailable. Preferably such compounds would also have the ability to cross the blood brain barrier and thus have brain exposure. Preferably such compounds would also have the ability to potentially overcome resistance to existing kynurenine inhibitors by having an alternate mechanism of action.

The present invention provides certain novel 2,3-dihydro-1H-indole compounds that are inhibitors of kynurenine production. The skilled person will appreciate that inhibitors of kynurenine production may have clinical utility as a single agent or in combination with other anti-cancer agents for the treatment of different types of cancers and in particular melanoma, acute myeloid leukemia, chronic lymphocytic leukemia, colorectal cancer, renal cell carcinoma, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma.

The present invention also provides a compound of the formula:

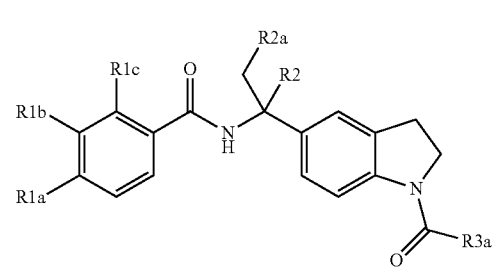

I wherein:
R1a is hydrogen, methyl, ethenyl, cyano, fluoro, chloro, fluoromethyl, or difluoromethyl;
R1b is hydrogen, fluoro, or chloro;
R1c is hydrogen, hydroxy, fluoro, benzyloxy, or hydroxyethylamino;
R2 is hydrogen or methyl;
R2a is hydrogen or methyl; and
R3a is tetrahydropyranyl.

The present invention provides a compound of the formula:

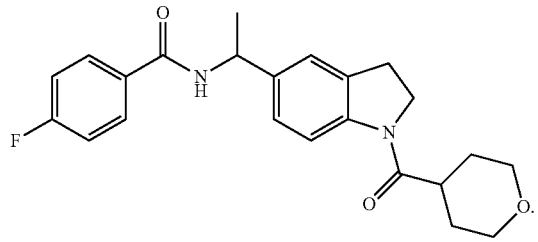 [SMILES: CC(NC(=O)c1ccc(F)cc1)c1ccc2c(c1)CCN2C(=O)C1CCOCC1]

The present invention also provides a compound of the formula:

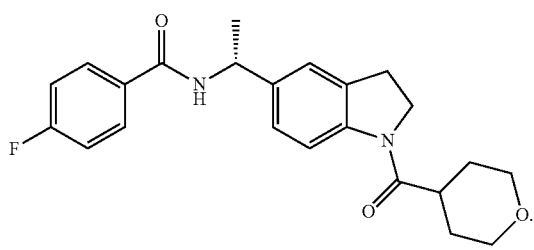

The present invention also provides a compound of the formula:

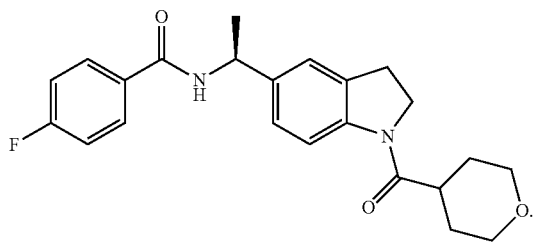 [SMILES: C[C@H](NC(=O)c1ccc(F)cc1)c1ccc2c(c1)CCN2C(=O)C1CCOCC1]

The present invention also provides a compound which is 4-fluoro-N-{(1R)-1-[1-(tetrahydro-2H-pyran-4-ylcarbonyl)-2,3-dihydro-1H-indol-5-yl]ethyl}benzamide. Preferably the compound is 4-fluoro-N-{(1R)-1-[1-(tetrahydro-2H-pyran-4-ylcarbonyl)-2,3-dihydro-1H-indol-5-yl]ethyl}benzamide in a crystalline form. Preferably the compound is crystalline 4-fluoro-N-{(1R)-1-[1-(tetrahydro-2H-pyran-4-ylcarbonyl)-2,3-dihydro-1H-indol-5-yl]ethyl}benzamide characterized by an X-ray powder diffraction pattern (Cu radiation, $\lambda$-1.54060 Å) comprising at least one peak at 17.38° in combination with one or more peaks selected from the group consisting of 12.51°, 15.65°, 16.37°, 17.56°, 21.48° and 25.23° (2θ±0.2°).

The present invention also provides an intermediate or salt thereof of the formula:

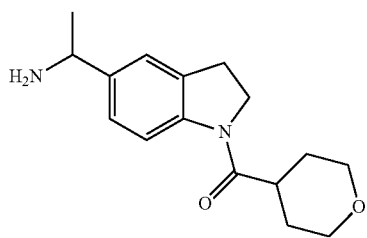

useful in the method of making certain compounds of the present invention.

The present invention also provides an intermediate or salt thereof of the formula:

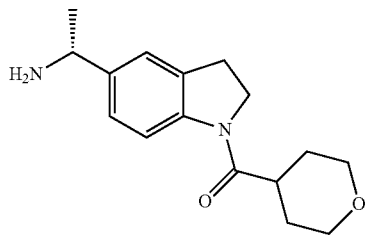

useful in the method of making certain compounds of the present invention.

The present invention also provides an intermediate or salt thereof of the formula:

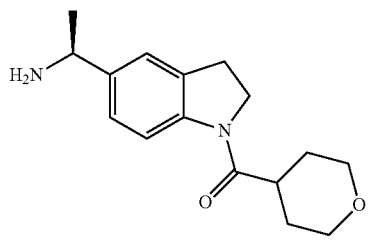 [SMILES: CC(N)c1ccc2c(c1)CCN2C(=O)C1CCOCC1]

useful in the method of making certain compounds of the present invention.

The present invention also provides an intermediate of the formula:

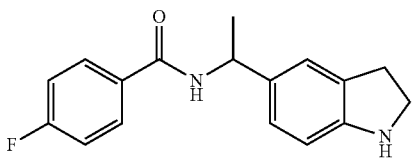 [SMILES: CC(NC(=O)c1ccc(F)cc1)c1ccc2c(c1)CCN2]

useful in the method of making certain compounds of the present invention.

The present invention also provides an intermediate of the formula:

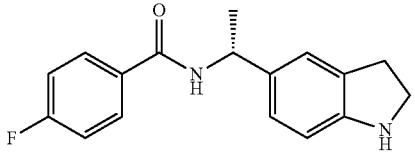 [SMILES: C[C@@H](NC(=O)c1ccc(F)cc1)c1ccc2c(c1)CCN2]

useful in the method of making certain compounds of the present invention.

The present invention also provides an intermediate of the formula:

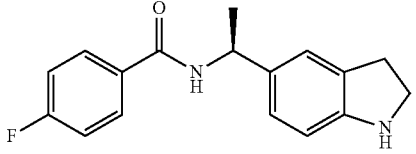 [SMILES: C[C@H](NC(=O)c1ccc(F)cc1)c1ccc2c(c1)CCN2]

useful in the method of making certain compounds of the present invention.

The present invention also provides a pharmaceutical composition comprising a compound of the present invention with a pharmaceutically acceptable excipient, carrier, or diluent. Preferably the compound is 4-fluoro-N-{(1R)-1-[1-(tetrahydro-2H-pyran-4-ylcarbonyl)-2,3-dihydro-1H-indol-5-yl]ethyl}benzamide.

The present invention provides a method of treating a patient with a cancer selected from the group consisting of melanoma, acute myeloid leukemia, chronic lymphocytic leukemia, colorectal cancer, renal cell carcinoma, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma comprising administering to the patient an effective amount of a compound of the present invention. Preferably the cancer is melanoma. Preferably the cancer is colorectal cancer. Preferably the cancer is renal cell carcinoma. Preferably the cancer is breast cancer. Preferably the cancer is lung cancer, in particular non-small cell lung cancer. Preferably the cancer is ovarian cancer. Preferably the cancer is glioma. Preferably the compound is 4-fluoro-N-{(1R)-1-[1-(tetrahydro-2H-pyran-4-ylcarbonyl)-2,3-dihydro-1H-indol-5-yl]ethyl}benzamide.

This invention also provides a compound of the present invention for use in therapy. Additionally, this invention provides a compound of the present invention for use in the treatment of a cancer selected from the group consisting of melanoma, acute myeloid leukemia, chronic lymphocytic leukemia, colorectal cancer, renal cell carcinoma, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma. Preferably the cancer is melanoma. Preferably the cancer is colorectal cancer. Preferably the cancer is renal cell carcinoma, Preferably the cancer is breast cancer. Preferably the cancer is lung cancer, in particular non-small cell lung cancer. Preferably the cancer is ovarian cancer. Preferably the cancer is glioma. Preferably the compound is 4-fluoro-N-{(1R)-1-[1-(tetrahydro-2H-pyran-4-ylcarbonyl)-2,3-dihydro-1H-indol-5-yl]ethyl}benzamide. Preferably the compound is 4-fluoro-N-{(1R)-1-[1-(tetrahydro-2H-pyran-4-ylcarbonyl)-2,3-dihydro-1H-indol-5-yl]ethyl}benzamide.

This invention also provides a combination comprising a compound of the present invention and LY3300054 for simultaneous, separate, or sequential use in the treatment of a cancer selected from the group consisting of non-small cell lung cancer and colon cancer. Preferably the cancer is non-small cell lung cancer. Preferably the cancer is colon cancer. Preferably the compound is 4-fluoro-N-{(1R)-1-[1-(tetrahydro-2H-pyran-4-ylcarbonyl)-2,3-dihydro-1H-indol-5-yl]ethyl}benzamide. Preferably the compound is 4-fluoro-N-{(1R)-1-[1-(tetrahydro-2H-pyran-4-ylcarbonyl)-2,3-dihydro-1H-indol-5-yl]ethyl}benzamide and the cancer is non-small cell lung cancer. Preferably the compound is 4-fluoro-N-{(1R)-1-[1-(tetrahydro-2H-pyran-4-ylcarbonyl)-2,3-dihydro-1H-indol-5-yl]ethyl}benzamide and the cancer is colon cancer.

The following paragraphs describe preferred classes of Formula I:
a) R1a is hydrogen, methyl, cyano, fluoro, or chloro;
b) R1b is hydrogen, fluoro, or chloro;
c) R1c is hydrogen or hydroxy;
d) R2 is hydrogen or methyl;
e) R2a is hydrogen or methyl;
f) R3a is tetrahydropyranyl; and
g) R1a is fluoro, R1b is hydrogen, R1c is hydrogen, R2 is hydrogen, R2a is hydrogen, and R3 is tetrahydropyranyl.

Certain of the compounds of the present invention are crystalline. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 38—National Formulary 35 Chapter <941> Characterization of crystalline and partially crystalline solids by X-ray powder diffraction (XRPD) Official May 1, 2015. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2-theta.

As used herein, "treat", "treating" or "treatment" refers to restraining, slowing, stopping, or reversing the progression or severity of an existing symptom or disorder.

As used herein, the term "patient" refers to a warm blooded animal such as a mammal, in particular a human, which is afflicted with a particular disease, disorder, or condition.

One of ordinary skill in the art will appreciate that compounds and certain intermediates of the invention can exist in tautomeric forms. When any reference in this application to one of the specific tautomers of the compounds of the invention is given, it is understood to encompass both tautomeric forms and all mixtures thereof.

Some intermediates or compounds of the present invention disclosed herein may have one or more chiral or stereogenic centers. All individual stereoisomers, enantiomers and diastereomers, as well as mixtures of the enantiomers and diastereomers of all of these aforementioned compounds or intermediates of the present invention are contemplated including racemates. It is preferred that compounds or intermediates of the present invention disclosed herein containing at least one chiral center exist as single enantiomers or diastereomers. The single enantiomer or diastereomer may be prepared beginning with chiral reagents or by stereoselective or stereospecific synthetic techniques (as illustrated in the preparations and examples). Alternatively, the single enantiomer or diastereomers may be isolated from mixtures by standard chiral chromatographic (as illustrated in the preparations and examples) or crystallization techniques. The skilled artisan will appreciate that in some circumstances the elution order of enantiomers or diastereomers may be different due to different chromatographic columns and mobile phases.

The designation of "Isomer 1" in a compound name represents that the corresponding intermediate or compound of the present invention is the first of two eluting enantiomers when a mixture of a pair of enantiomers is separated by chiral chromatography. The designation of "Isomer 2" in a compound name represents that the corresponding intermediate or compound of the present invention is the second of two eluting enantiomers when the mixture of a pair of enantiomers is separated by chiral chromatography.

The designation of "Isomer A" in a compound name represents that the corresponding intermediate or compound of the present invention is a single isomer from a chiral synthesis of unknown absolute configuration.

As used herein, "LY3300054" is an antibody that binds human PD-L1 (SEQ ID NO: 1), comprising a light chain (LC) and a heavy chain (HC), wherein the light chain comprises a light chain variable region (LCVR) and the heavy chain comprises a heavy chain variable region (HCVR), and wherein the LCVR comprises light chain complementarity determining regions LCDR1, LCDR2, and LCDR3, where the amino acid sequence of LCDR1 is SGSSSNIGSNTVN (SEQ ID NO: 5), the amino acid sequence of LCDR2 is YGNSNRPS (SEQ ID NO: 6), and the amino acid sequence of LCDR3 is QSYDSSLSGSV (SEQ ID NO: 7), and wherein the HCVR comprises heavy chain complementarity determining regions HCDR1, HCDR2, and HCDR3, where the amino acid sequence of HCDR1 is KASGGTFSSYAIS (SEQ ID NO: 2), the amino acid sequence of HCDR2 is GIIPIFGTANYAQKFQG (SEQ ID NO: 3), and the amino acid sequence of HCDR3 is ARSPDYSPYYYYGMDV (SEQ ID NO: 4), respectively.

In some embodiments of LY3300054, the LY3300054 binds to human PD-L1, and comprises a light chain (LC) and a heavy chain (HC), wherein the light chain comprises a light chain variable region (LCVR) and the heavy chain comprises a heavy chain variable region (HCVR), wherein the amino acid sequence of the LCVR is SEQ ID NO: 9, and the amino acid sequence of the HCVR is SEQ ID NO: 8. In some embodiments of LY3300054, the LY3300054 binds to human PD-L1, comprising a light chain (LC) and a heavy chain (HC), wherein the amino acid sequence of the LC is SEQ ID NO: 10 and the HC has the amino acid sequence given in SEQ ID NO: 11. In an embodiments of LY3300054, the LY3300054, comprises two light chains and two heavy chains, wherein each light chain has the amino acid sequence given in SEQ ID NO: 11, and each heavy chain has the amino acid sequence given in SEQ ID NO: 10.

As used herein, the term "light chain variable region" or "LCVR" means a portion of a light chain of an antibody molecule that includes amino acid sequences of CDRs and FRs.

As used herein, the term "heavy chain variable region" "HCVR" means a portion of a heavy chain of an antibody molecule that includes amino acid sequences of CDRs and FRs.

As used herein, the terms "complementarity determining region" and "CDR", mean the non-contiguous antigen combining sites found within the variable region of LC and HC polypeptides of an antibody or an antigen-binding fragment thereof. These particular regions have been described by others including Kabat, et al., Ann. NY Acad. Sci. 190:382-93 (1971); Kabat et al., J. Biol. Chem. 252:6609-6616 (1977); Kabat, et al., Sequences of Proteins of Immunological Interest, Fifth Edition, U.S. Department of Health and Human Services, NIH Publication No. 91-3242 (1991); Chothia, et al., J. Mol. Biol. 196:901-917 (1987); MacCallum, et al., J. Mol. Biol., 262:732-745 (1996); and North, et al., J. Mol. Biol., 406, 228-256 (2011), where the definitions include overlapping or subsets of amino acid residue when compared against each other.

The CDRs are interspersed with regions that are more conserved, termed framework regions ("FR"). Each LCVR and HCVR is composed of three CDRs and four FRs, arranged from amino-terminus to carboxy-terminus in the following order: FR1, CDR1, FR2, CDR2, FR3, CDR3, FR4. The three CDRs of the light chain are referred to as "LCDR1, LCDR2, and LCDR3" and the three CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions is in accordance with known conventions (e.g., Kabat (1991), Chothia (1987), and/or North (2011)). In different embodiments of the invention, the FRs of the LY3300054 may be identical to the human germline sequences, or may be naturally or artificially modified.

As used herein, the term "$K_D$" means the equilibrium dissociation constant of a particular antibody-antigen or antibody fragment-antigen interaction.

As used herein, the term "binds" means the affinity of an antibody for human PD-L1 is intended to mean, unless indicated otherwise, a $K_D$ of less than about $1 \times 10^{-6}$ M, preferably, less than about $1 \times 10^{-9}$ M as determined by common methods known in the art, including by use of a surface plasmon resonance (SPR) biosensor at 37° C. essentially as described herein.

As used herein, the following terms have the meanings indicated: "ACN" refers to acetonitrile; "APCI" refers to atmospheric pressure chemical ionization; "BTI" refers to [bis(trifluoroacetoxy)iodo]benzene; "CDI" refers to carbonyldiimidazole; "DCM" refers to dichloromethane; "DMSO" refers to dimethyl sulfoxide; "DMF" refers to N,N-dimethylformamide; "DPBS" refers to Dulbecco's phosphate-buffered saline; "ES" refers to electrospray ionization; "EtOAc" refers to ethyl acetate; "EtOH" refers to ethanol; "FBS" refers to fetal bovine serum; "HPLC" refers to high performance liquid chromatography; "iPrOH" refers to isopropanol; "LC/MS-MS" refers to liquid chromatography tandem mass spectrometry; "L-kynurenine-d4" refers to (2S)-2-amino-4-(2-amino-3,4,5,6-tetradeuterio-phenyl)-4-oxo-butanoic acid; "MES" refers to 2-(N-morpholino)ethanesulfonic acid; "MS" refers to mass spectroscopy; "MeOH" refers to methanol; "PBS" refers to phosphate-buffered saline; "TFA" refers to trifluoroacetic acid; "TEA" refers to triethylamine; "THF" refers to tetrahydrofuran; "SFC" refers to supercritical fluid chromatography; and "UVW" refers to ultra-violet wavelength.

The compounds of the present invention can be prepared according to the following schemes, preparations and examples by methods well known and appreciated in the art. Suitable reaction conditions for the steps of these preparations and examples are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

Compounds of the present invention may be synthesized as illustrated in the following schemes, where R1a, R1b, R1c, R2, R2a and R3a are as previously defined.

Scheme 1: Synthesis of compounds of Formula I

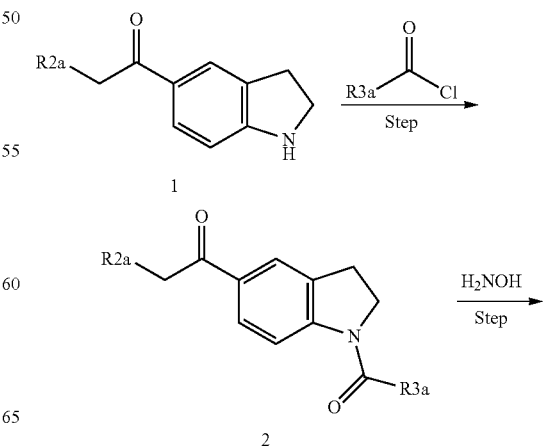

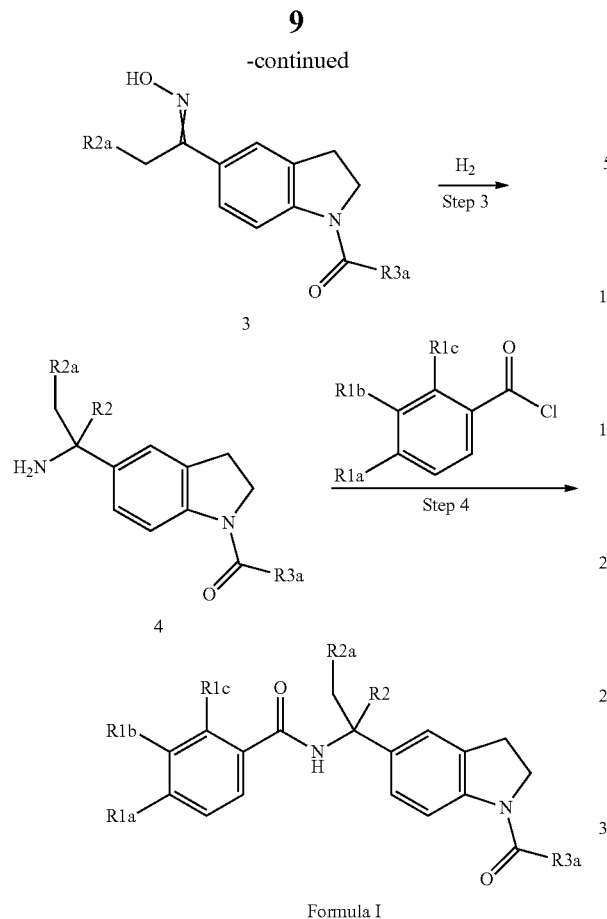

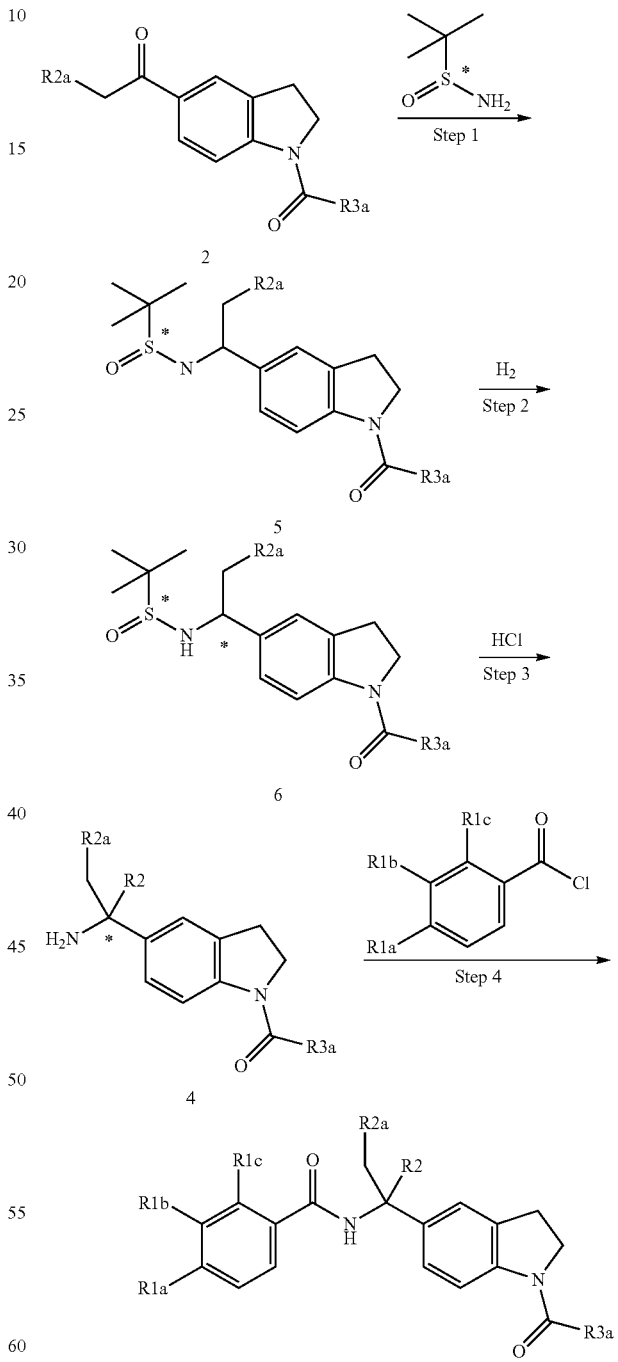

resolved by one of ordinary skill in the art at any convenient point in the synthesis of compounds of the present invention by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994).

Scheme 1 illustrates the general synthesis of compounds of Formula I, R2 is H. In Step 1, a 2,3-dihydro-1H-indole (Compound 1) is reacted with an appropriate activated carboxylic acid such as an acid chloride in the presence of a suitable base such as TEA and in a suitable solvent such as DCM or dichloroethane (DCE) at an appropriate temperature such as 0° C. to refluxing. A skilled artisan will appreciate that there are many activated carboxylic acids and many methods to activate carboxylic acids in situ to accomplish the reaction of Step 1. The resulting ketone (Compound 2) of Step 1 is then treated with hydroxylamine in a polar protic solvent such as EtOH at an appropriate temperature such as room temperature to refluxing to give the oxime as a mixture of E and Z isomers (Compound 3). Step 3 shows the reduction of the oxime (Compound 3) to the amine (Compound 4). The skilled artisan will appreciate that there are many methods available to affect this transformation. For example, the oxime (Compound 3) is contacted with an appropriate catalyst such as RANEY® nickel in an appropriate solvent such as MeOH or EtOH in an appropriate reactor such as a PARR® shaker. The mixture is then subjected to hydrogen pressure such as 100-500 kPa at an appropriate temperature such as room temperature to 50° C. for an appropriate time such as one to 24 hours. Scheme 1, Step 4 depicts the amide coupling of the amine (Compound 4) with an appropriate activated carboxylic acid such as an acid chloride in the presence of a suitable base such as TEA and in a suitable solvent such as DCM or DCE at an appropriate temperature such as 0° C. to refluxing to give a compound of Formula I. A skilled artisan will appreciate that there are many activated carboxylic acids and many methods to activate carboxylic acids in situ to accomplish the reaction of Step 4. The skilled artisan will further appreciate that Scheme 1, Step 3 and Step 4 result in products with chiral centers. Individual enantiomers may be separated or Scheme 2 illustrates an alternate general synthesis of compounds of Formula I, R2 is H. In Step 1, the ketone (Compound 2) is reacted with an appropriate chiral sulfinamide in the presence of an appropriate Lewis acid such as titanium(IV) ethoxide in an appropriate solvent such as THF at an appropriate temperature such as room temperature to reflux for an appropriate time such as one to 24 hours to give a chiral ethylidenesulfinamide (Compound 5). A skilled artisan will appreciate that reagents are available to generate either enantiomer of the sulfinamide (Compound 5). Chiral reduction is depicted in Step 2 to generate an ethylsulfinamide (Compound 6) from an ethylidinesulfinamide (Compound 5) and asterisks are used to indicate chiral centers for clarity. For example, an appropriate catalyst is pre-formed by mixing an appropriate ruthenium reagent such as dichloro(p-cymene)ruthenium(II) dimer with an appropriate aminoethanol such as 2-amino-2-methyl-1-propanol in an appropriate solvent such as iPrOH in the presence of a water scavenger such as 4 Å molecular sieves at an appropriate temperature such as room temperature to refluxing for an appropriate time such as five minutes to approximately one hour. The preformed catalyst reaction is cooled to an appropriate temperature such as room temperature to 50° C. and treated with an ethylidenesulfinamide (Compound 5) and an appropriate base such as potassium tert-butoxide. The reaction is maintained at an appropriate temperature such as room temperature to 50° C. for an appropriate time such as one to 24 hours. The skilled artisan will appreciate that there are many catalytic and stoichiometric methods that will affect the same transformation and that these methods can result in diastereomeric enrichment depending on the nature of the substrates and the reagents used, up to and including generation of a single diastereomer. Acid hydrolysis of a ethylsulfinamide (Compound 6) can be affected by treatment with an appropriate acid such as hydrochloric acid (HCl) in an appropriate solvent such as dioxane, iPrOH, EtOAc or MeOH at an appropriate temperature such as 0° C. to room temperature for an appropriate time such as one to eight hours to give an amine (Compound 4). The skilled artisan will appreciate that many methods for isolation are known and these can result in isolation of either the salt or free base of the amine (Compound 4). Step 4 depicts the amide coupling of an amine (Compound 4) with an appropriate activated carboxylic acid analogous to Scheme 1, Step 4 above to give a compound of Formula I.

Scheme 3: Synthesis of compounds of Formula I

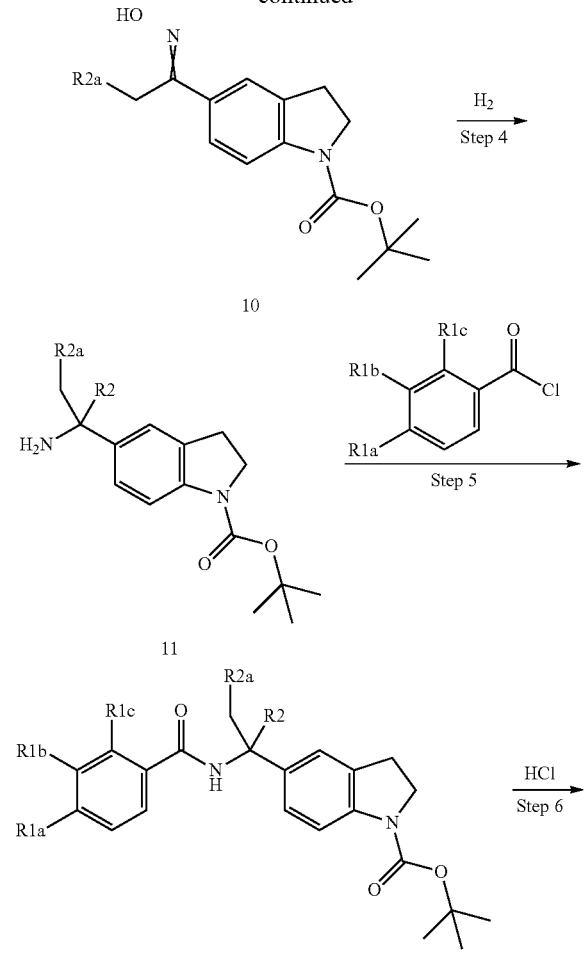

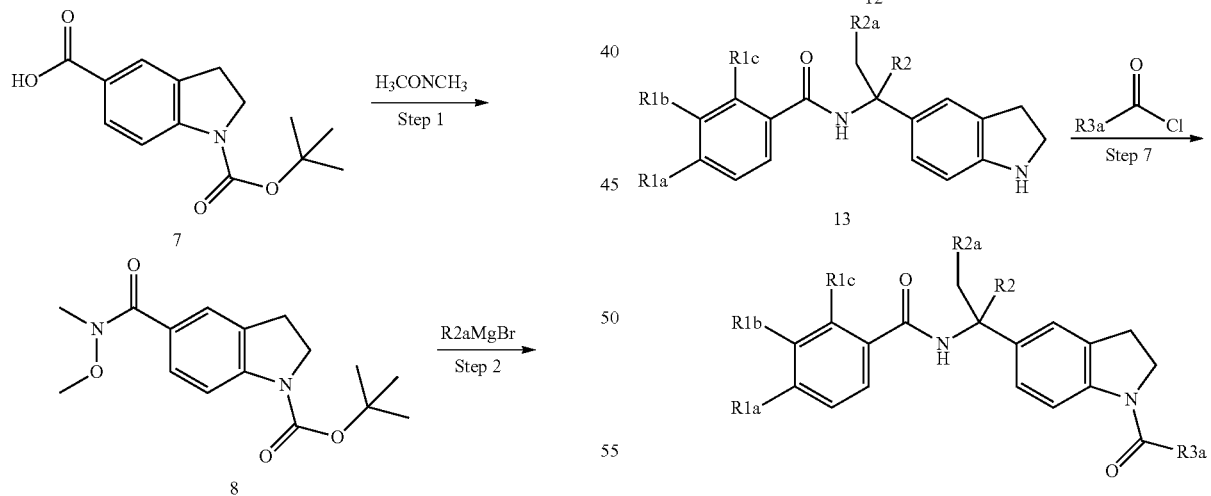

Scheme 3 depicts an alternate general synthesis of a compound of Formula I, R2 is H. Step 1 depicts an amide coupling of a carboxylic acid (Compound 7) with N,O-dimethylhydroxylamine hydrochloride to give a Weinreb amide (Compound 8). The skilled artisan will appreciate that there are many methods to affect this transformation. For example, a carboxylic acid (Compound 7) can be treated with an appropriate coupling reagent such as 1-[bis(dimethylamino)methylene]-1H-1,2,3-triazolo[4,5-b]pyridinium-3- oxid hexafluorophosphate (HATU) in the presence of an appropriate base such as N,N-diisopropylethylamine in an appropriate solvent such as DMF for an appropriate time such as five to ten minutes. The mixture is then treated with N,O-dimethylhyrdoxylamine hydrochloride and the mixture is stirred at an appropriate temperature such as room temperature to 100° C. for an appropriate time such as three to 18 hours. The resulting Weinreb amide (Compound 8) is then treated with an appropriate Grignard, alkyl lithium or alkyl zinc reagent, in Step 2, to give a ketone (Compound 9). The skilled artisan will appreciate that there are a large number of methods available to affect this transformation. For example, the Weinreb amide (Compound 8) in an appropriate solvent such as THF at an appropriate temperature such as 0° C. to −78° C. is treated with an appropriate alkyl metal reagent such as ethylmagnesium bromide. The reaction is continued after the addition for an appropriate time such as one to 18 hours to give a ketone (Compound 9). Steps 3, 4 and 5 of Scheme 3 are presented for clarity. The methods are analogous to those presented in Scheme 1, Steps 2, 3 and 4 respectively. One of skill in the art will appreciate that compound 11 contains a chiral center and that chiral purification can be performed on compound 11 or the racemic mixture can be carried forward and separation can be performed after any of the subsequent steps. Step 6 depicts the deprotection of the tert-butoxycarbonyl protecting group of a carbamate (Compound 12) to give an amine (Compound 13). A skilled artisan will appreciate that this transformation can be conducted under acid, base or thermal conditions. For example, a carbamate (Compound 12) is contacted with an appropriate acid such as HCl in an appropriate solvent such as dioxane or DCM or a mixture thereof at an appropriate temperature such as 0° C. to refluxing for an appropriate time such as one to 18 hours to give an amine (Compound 13). The skilled artisan will appreciate that there are methods to isolate an amine as a salt or freebase. Step 7 depicts the amide coupling of an amine (Compound 13) and an activated carboxylic acid to give a compound of Formula I. The conditions are analogous to those presented in Scheme 1, Step 1.

Scheme 4: Synthesis of compounds of Formula I

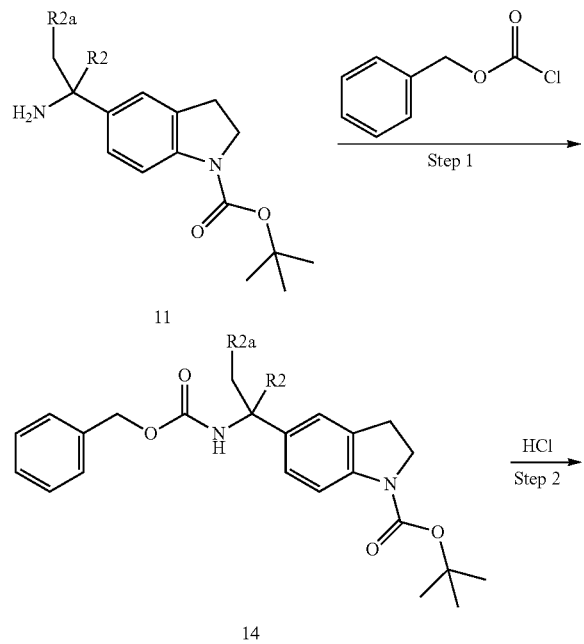

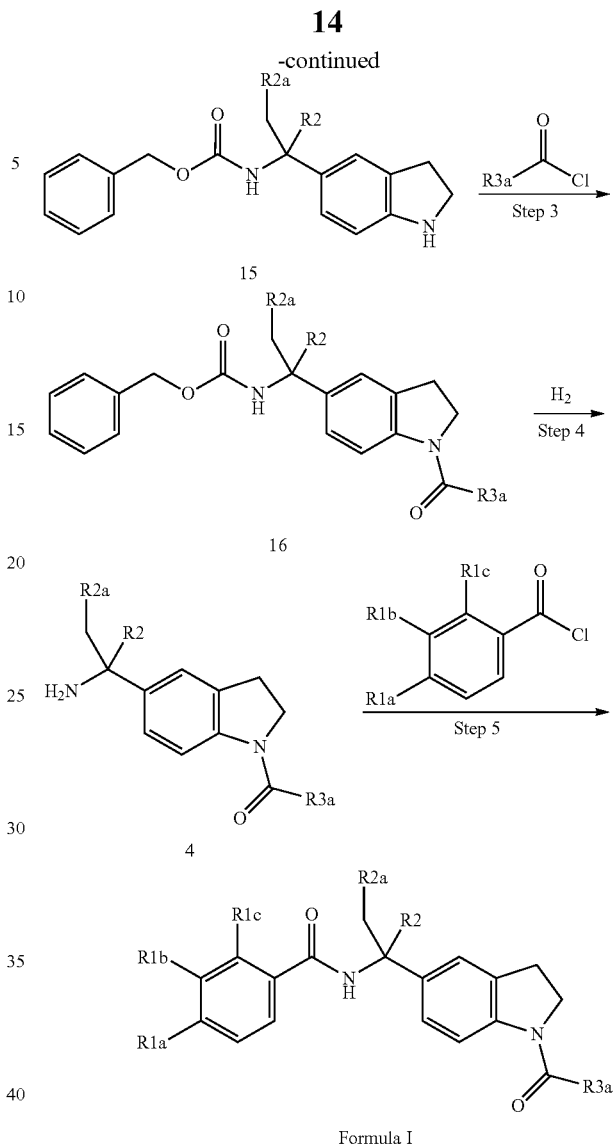

Scheme 4 depicts an alternate general synthesis of a compound of Formula I. Step 1 depicts the protection of an amine (Compound 11) with a benzyl carbamate protecting group to give a carbamate (Compound 14). A skilled artisan will appreciate that there are many amine protecting groups available that would be orthogonal protecting groups to the tert-butoxycarbonyl group on compound 14. In an example procedure, an amine (Compound 11) in an appropriate solvent such as DCM and in the presence of a suitable base such as N,N-diisopropylethylamine is contacted with benzyloxychloroformate at an appropriate temperature such as 0° C. to room temperature for an appropriate time such as one to 18 hours. The tert-butoxycarbonyl protecting group of Compound 14 is selectively deprotected to give an amine (Compound 15) utilizing methods analogous to those described for Scheme 3, Step 6. The resulting amine (Compound 15) is then subjected to an amide coupling reaction with an activated carboxylic acid by methods analogous to those in Scheme 1, Step 1 to give an amide (Compound 16). Step 4 depicts the deprotection of the benzyloxy carbamate protecting group of compound 16 to give an amine (Compound 4). A skilled artisan will appreciate that a variety of methods are available to affect this transformation. For example, compound 16 is subjected to catalytic hydrogenation with an appropriate catalyst such as palladium hydroxide in an appropriate solvent such as EtOH under an appropriate hydrogen pressure such as 100 to 500 kPa for an appropriate time such as one to eight hours to give the amine (Compound 4). Finally, the conversion of amine (Compound 4) to a compound of Formula I is as described in Scheme 1, Step 4.

Scheme 5: Synthesis of compounds of Formula I

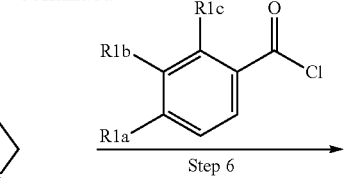

Scheme 5 depicts an alternate general synthesis of a compound of Formula I. Step 1 depicts the amide coupling of an amine (Compound 17) and an activated carboxylic acid to give an amide (Compound 18). The conditions are analogous to those presented in Scheme 1, Step 1. Step 2 depicts the formation of alpha aryl ester (Compound 19) through the catalytic cross coupling of a bromide (Compound 18) with an ester enolate. The skilled artisan will appreciate the wide range of conditions that can affect this transformation. For example, a solution of an appropriate dialkyl amine such as dicyclohexylamine in an appropriate solvent such as toluene is treated with an appropriate lithium base such as n-butyllithium at an appropriate temperature such as 0° C. to −78° C. for an appropriate time such as 10 minutes to one hour. This solution is treated with a solution of an appropriate ester such as methyl 2-methylpropanoate in an appropriate solvent such as toluene and the resulting mixture is stirred for an appropriate time such as 10 minutes to one hour at an appropriate temperature such as 0° C. to −40° C. The resulting mixture is then treated with an appropriate palladium catalyst such as di-μ-bromobis(tri-t-butylphosphine)dipalladium(I) and the mixture is stirred at an appropriate temperature such as 0° C. to room temperature for an appropriate time such as one to 18 hours to give an alpha aryl ester (Compound 19). An ester (Compound 19) can be hydrolyzed to an acid (Compound 20) by methods well known in the art. For example, an ester (Compound 19) is contacted with a suitable base such as potassium trimethylsilanolate in an appropriate solvent such as THF at an appropriate temperature such as room temperature to refluxing for an appropriate time such as one to seven days. Step 4 depicts the amide coupling of a carboxylic acid (Compound 20) with ammonia to give a carboxamide (Compound 21). The skilled artisan will appreciate the many methods available to active a carboxylic acid as well as introduce ammonia sources. For example, a carboxylic acid (Compound 20) is contacted with 1,1'-carbonyldiimidazole in an appropriate solvent such as DCM or DMF or a mixture thereof at an appropriate temperature such as 0° C. to refluxing for an appropriate time such as 30 minutes to eight hours. Ammonium hydroxide is added to the mixture and the reaction is continued for an additional time such as one to 18 hours. Step 21 depicts the Hoffman rearrangement of a carboxamide (Compound 21) to an amine (Compound 4). The skilled artisan will appreciate the wide variety of reagents and conditions that can affect this transformation. For example, a solution of a carboxamide (Compound 21) in an appropriate solvent such as a mixture of ACN and water is treated with [bis(trifluoroacetoxy)iodo]benzene at appropriate temperature such as room temperature to refluxing for an appropriate time such as one to 18 hours. Finally, the conversion of amine (Compound 4) to a compound of Formula I is describe in Scheme 1, Step 4.

Preparation 1

Synthesis of 1-[1-(tetrahydro-2H-pyran-4-ylcarbonyl)-2,3-dihydro-1H-indol-5-yl]ethanone Add TEA (51.9 mL, 372.2 mmol) and tetrahydropyran-4-carbonyl chloride (22.1 g, 148.9 mmol) to a mixture of 1-indolin-5-ylethanone (20.0 g, 124.1 mmol) in DCM (496 mL). Stir the resulting mixture at room temperature for two hours. Dilute the reaction mixture with DCM (500 mL) and wash with saturated aqueous sodium bicarbonate. Isolate the organic layer and extract the aqueous layer twice with DCM (500 mL). Wash combined organic layers with saturated aqueous sodium chloride, dry over anhydrous sodium sulfate, filter and concentrate the filtrate to give the title compound quantitatively as a light yellow solid. ES/MS (m/z): 274.0 (M+H).
Alternative Isolation Procedure:
Treat the product with heptane and concentrate. Repeat the treatment and concentration a second time. Treat with heptane and cool to 0-5° C. Collect the product by filtration and rinse with heptane and dry to give the title compound.

Preparation 2

Synthesis of [5-(N-hydroxyethanimidoyl)-2,3-dihydro-1H-indol-1-yl](tetrahydro-2H-pyran-4-yl)methanone Add hydroxylamine (50 mass % in water, 22.8 mL, 372 mmol) to a mixture of 1-[1-(tetrahydro-2H-pyran-4-ylcarbonyl)-2,3-dihydro-1H-indol-5-yl]ethanone (Preparation 1) (33.9 g, 124.0 mmol) in EtOH (1240 mL). Stir the resulting mixture at room temperature for three days. Concentrate the reaction mixture to give the title compound as a mixture of E/Z isomers quantitatively. ES/MS (m/z): 289.0 (M+H).

Preparation 3

Synthesis of racemic [5-(1-aminoethyl)-2,3-dihydro-1H-indol-1-yl](tetrahydro-2H-pyran-4-yl)methanone Add RANEY® nickel (slurry in EtOH, 60 g) to a 2250 mL PARR® shaker bottle and purge with nitrogen. Add 2M ammonia in MeOH (700 mL) and then a solution of [5-(N-hydroxyethanimidoyl)-2,3-dihydro-1H-indol-1-yl](tetrahydro-2H-pyran-4-yl)methanone (Preparation 2) (35.8 g, 124.0 mmol) in 2M ammonia in MeOH (700 mL). Cool the potentially exothermic mixture to room temperature if necessary, seal, purge with nitrogen and then hydrogen. Stir under hydrogen (60 psi, or 414 kPa) for four hours at room temperature. Filter off the solids and concentrate the filtrate. Purify by silica gel column chromatography with 7-26% (7M ammonia in MeOH) in EtOAc to give the title compound (26.5 g, 78%) as an off-white solid. ES/MS (m/z): 275.0 (M+H).

Preparation 4A and B

Separation of [5-(1-aminoethyl)-2,3-dihydro-1H-indol-1-yl](tetrahydro-2H-pyran-4-yl)methanone, Isomer 1 and [5-(1-aminoethyl)-2,3-dihydro-1H-indol-1-yl](tetrahydro-2H-pyran-4-yl)methanone, Isomer 2

Purify racemic [5-(1-aminoethyl)-2,3-dihydro-1H-indol-1-yl](tetrahydro-2H-pyran-4-yl)methanone (Preparation 3) by chiral SFC to afford the first eluting enantiomer (Isomer 1). ES/MS (m/z): 275.0 (M+H). Purification conditions: CHIRALPAK® AD-H, 50×150 cm column; Mobile phase: 40% EtOH (containing 0.5% N,N-dimethylethylamine) in $CO_2$; Column temperature: 40° C.; Flow rate: 300 g/minute; UVW: 260 nm. Confirm enantiomeric enrichment of Isomer 1 by chiral analytical SFC (>99% ee, $R_t$: 1.35 minutes; Column: CHIRALPAK® AD-H, 4.6×150 mm; Mobile phase: 40% EtOH (containing 0.5% N,N-dimethylethylamine) in $CO_2$; Flow rate: 5 mL/minute; UVW: 260 nm) or by chiral analytical HPLC (97.4% ee, $R_t$: 6.48 minutes; Column: CHIRALPAK® AD-H, 4.6 mm×150 mm; Mobile phase: 100% EtOH (containing 0.2% isopropylamine); Flow rate: 1 mL/minute; UVW: 225 nm).

The above purification also yields the second eluting enantiomer (Isomer 2). ES/MS (m/z): 275.1 (M+H). Confirm enantiomeric enrichment of Isomer 2 by chiral analytical SFC (97.2% ee, $R_t$: 1.85 minutes; Column: CHIRALPAK® AD-H, 4.6×150 mm; Mobile phase: 40% EtOH (containing 0.5% N,N-dimethylethylamine) in $CO_2$; Flow rate: 5 mL/minute; UVW: 260 nm) or by chiral analytical HPLC (97.6% ee, $R_t$: 5.31 minutes; Column: CHIRALPAK® AD-H, 4.6 mm×150 mm; Mobile phase: 100% EtOH (containing 0.2% isopropylamine); Flow rate: 1 mL/minute; UVW: 225 nm).

Preparation 5

Synthesis of (R)-2-methyl-N-{1-[1-(tetrahydro-2H-pyran-4-ylcarbonyl)-2,3-dihydro-1H-indol-5-yl]ethylidene}propane-2-sulfinamide Add titanium(IV) ethoxide (5.0 g, 21.9 mmol) to a mixture of 1-[1-(tetrahydro-2H-pyran-4-ylcarbonyl)-2,3-dihydro-1H-indol-5-yl]ethanone (Preparation 1) (3.0 g, 11.0 mmol) and (R)-2-methylpropane-2-sulfinamide (1.6 g, 13.2 mmol) in THF (43.9 mL). Reflux the resulting mixture for 24 hours. Cool the reaction mixture to room temperature. Dilute the mixture with EtOAc (100 mL) and saturated aqueous sodium chloride (40 mL) and stir vigorously for 15 minutes. Isolate the organic layer and extract the aqueous layer twice with EtOAc (100 mL). Wash the combined organic layers with saturated aqueous sodium chloride, dry over anhydrous sodium sulfate, filter and concentrate the filtrate. Purify by silica gel column chromatography with 10-100% ACN in DCM to give the title compound (3.7 g, 87%) as a light yellow solid. ES/MS (m/z): 377.0 (M+H).
Alternative Isolation Procedure:
Instead of cooling the reaction to room temperature, cool the reaction mixture to 10° C. and then filter. Rinse the solid with toluene and dry to give the title compound.

Preparation 6

Synthesis of (R)-2-methyl-N-{1-[1-(tetrahydro-2H-pyran-4-ylcarbonyl)-2,3-dihydro-1H-indol-5-yl]ethyl}propane-2-sulfinamide, Isomer A Heat a mixture of dichloro(p-cymene)ruthenium(II) dimer (0.021 g, 0.033 mmol), 2-amino-2-methyl-1-propanol (0.006 g, 0.066 mmol) and molecular sieves (4 Å, 0.5 g) in iPrOH (2 mL) to reflux and then cool to 50° C. Add a solution of (R)-2-methyl-N-{1-[1-(tetrahydro-2H-pyran-4-ylcarbonyl)-2,3-dihydro-1H-indol-5-yl]ethylidene}propane-2-sulfinamide (Preparation 5) (0.5 g, 1.33 mmol) in iPrOH (8.8 mL) and a solution of potassium tert-butoxide (0.019 g, 0.17 mmol) in iPrOH (1.6 mL). Heat the resulting mixture at 55° C. for two hours. Then heat an additional mixture of dichloro(p-cymene)ruthenium(II) dimer (0.021 g, 0.033 mmol), 2-amino-2-methyl-1-propanol (0.06 g 0.66 mmol) and molecular sieves (4 Å, 0.5 g) in iPrOH (2 mL) to reflux, cool to 50° C. and add to the above reaction mixture. Add a solution of potassium tert-butoxide (0.019 g, 0.17 mmol) in iPrOH (1.6 mL) to the above reaction mixture. Heat the mixture at 55° C. for 20 minutes. Cool the reaction to room temperature and stir overnight. Dilute the reaction with DCM (20 mL) and filter through a diatomateous earth pad. Wash the pad with 5% MeOH in DCM and concentrate the filtrate to give the title compound quantitatively. ES/MS (m/z): 379.0 (M+H).

Alternative Isolation Procedure:

Instead of cooling the reaction to room temperature, cool the reaction mixture to 28-32° C. and then filter through diatomaceous earth. Rinse the filtering solid with dichloromethane and concentrate to give the title compound.

Preparation 7A and 7B

Synthesis of [5-(1-aminoethyl)-2,3-dihydro-1H-indol-1-yl](tetrahydro-2H-pyran-4-yl)methanone, Isomer 1

Add hydrochloric acid (4 M in 1,4-dioxane, 1.66 mL, 6.64 mmol) to a mixture of (R)-2-methyl-N-{1-[1-(tetrahydro-2H-pyran-4-ylcarbonyl)-2,3-dihydro-1H-indol-5-yl]ethyl}propane-2-sulfinamide, Isomer A (Preparation 6) (503 mg, 1.33 mmol) in MeOH (6.6 mL). Stir the resulting mixture at room temperature for one hour. Concentrate and purify the residue by reverse phase chromatography (Redisep Rf Gold High Performance C18 Reverse Phase Column, 0-100% ACN in 10 mM aqueous ammonium bicarbonate). Concentrate to give the title compound (265 mg, 73%). Confirm enantiomeric enrichment by chiral analytical HPLC (98.8% ee, $R_t$: 6.40 minutes; Column: CHIRALPAK® AD-H, 4.6 mm×150 mm; Mobile phase: 100% EtOH (containing 0.2% isopropylamine); Flow rate: 1 mL/minute; UVW: 225 nm). Confirmed to be preparation 4A, Isomer 1. ES/MS (m/z): 275.0 (M+H).

Synthesis of [5-(1-aminoethyl)-2,3-dihydro-1H-indol-1-yl](tetrahydro-2H-pyran-4-yl)methanone hydrochloride, Isomer 1

Add hydrochloric acid (5.5 M in iPrOH, 400 mL, 2.20 mol) to a 5° C. slurry of (R)-2-methyl-N-{1-[1-(tetrahydro-2H-pyran-4-ylcarbonyl)-2,3-dihydro-1H-indol-5-yl]ethyl}propane-2-sulfinamide, Isomer A (162.3 g, 364 mmol) in EtOAc (1.2 L) dropwise with overhead mechanical stirring. Remove cooling bath after addition of 100 mL of the acid solution. Continue the addition and stir the resulting mixture at room temperature for three hours. Cool to 3° C. and filter. Rinse the filter cake with 1-1.5 L of EtOAc, until washes are clear. Dry the collected solids in a house vacuum oven at 60° C. to give the title compound as an off white solid (96.4 g, 82.5%). Confirm enantiomeric enrichment by chiral analytical HPLC (98% ee, $R_t$: 6.45 minutes; Column: CHIRALPAK® AD-H, 4.6 mm×150 mm; Mobile phase: 100% EtOH (containing 0.2% isopropylamine); Flow rate: 1 mL/minute; UVW: 225 nm). Confirmed to be preparation 4A, Isomer 1. ES/MS (m/z): 275.0 (M+H). Confirmed to be preparation 4A, Isomer 1. ES/MS (m/z): 275.1 (M+H).

Prepare the following compounds essentially analogous to Preparation 1.

| Prep No. | Chemical Name | Physical data |
| --- | --- | --- |
| 8 | [5-Bromo-2,3-dihydro-1H-indol-1-yl](tetrahydro-2H-pyran-4-yl)methanone | ES/MS (m/z, $^{79}$Br/$^{81}$Br): 310.0/312.0 (M + H) |
| 9 | Benzyl {1-[1-(tetrahydro-2H-pyran-4-ylcarbonyl)-2,3-dihydro-1H-indol-5-yl]propyl}carbamate, Isomer A | ES/MS (m/z): 423.2 (M + H) |

Preparation 10

Synthesis of tert-butyl 5-acetyl-2,3-dihydro-1H-indole-1-carboxylate

Treat a 100° C. solution of 1-indolin-5-ylethanone (1.00 g, 6.02 mmol) in toluene (12 mL) with a solution of di-tert-butyl dicarbonate (1.97 g, 9.03 mmol) in toluene (12 mL) dropwise over 20 minutes. Continue heating the mixture for 30 minutes. Concentrate the reaction mixture. Purify by silica gel column chromatography with 15-35% (1:1 EtOAc:DCM) in hexanes to give the title compound (1.52 g, 97%) as a white solid. ES/MS (m/z): 262.0 (M+H).

Preparation 11

Synthesis of tert-butyl 5-[methoxy(methyl)carbamoyl]-2,3-dihydro-1H-indole-1-carboxylate Treat a solution of 1-(tert-butoxycarbonyl)-2,3-dihydro-1H-indole-5-carboxylic acid (14.0 g, 53.2 mmol) in DMF (200 mL) and N,N-diisopropylethylamine (28.0 mL, 161 mmol) with 1-[bis(dimethylamino)methylene]-1H-1,2,3-triazolo[4,5-b]pyridinium-3-oxid hexafluorophosphate (23.3 g, 61.1 mmol). Stir the resulting mixture at room temperature for five minutes. Add N,O-dimethylhydroxylamine hydrochloride (7.26 g, 74.4 mmol). Stir the resulting mixture overnight at room temperature. Dilute the reaction mixture with EtOAc and wash with saturated aqueous sodium bicarbonate. Isolate the organic layer and extract the aqueous layer twice with EtOAc. Wash the combined organic layers twice with water, adding saturated aqueous sodium chloride to aid phase separation. Dry the organic layer over anhydrous sodium sulfate, filter and concentrate the filtrate. Purify by silica gel column chromatography with 10-32% acetone in hexanes to give the title compound as a clear, colorless, thick oil in quantitative yield. ES/MS (m/z): 307.0 (M+H).

Preparation 12

Synthesis of tert-butyl 5-propanoyl-2,3-dihydro-1H-indole-1-carboxylate

Cool a solution of tert-butyl 5-[methoxy(methyl)carbamoyl]-2,3-dihydro-1H-indole-1-carboxylate (Preparation 11) (14.3 g, 46.7 mmol) in THF (311 mL, anhydrous) to 0° C. Add ethylmagnesium bromide (3M in diethylether, 39.0 mL, 117 mmol) dropwise over 25 minutes. After stirring at 0° C. for 1.5 hours, cautiously quench the reaction mixture with saturated aqueous ammonium chloride solution. Extract three times with EtOAc. Dry the combined organic layers over anhydrous sodium sulfate, filter and concentrate the filtrate. Purify by silica gel column chromatography with 15-30% (1:1 EtOAc:DCM) in hexanes to give the title compound (11.7 g, 91%) as a white solid. ES/MS (m/z): 276.0 (M+1).

Prepare the following compounds essentially analogous to Preparation 2, except Preparation 14, in which heating at 70° C. increases the reaction rate.

| Prep No. | Chemical Name | Physical data |
|---|---|---|
| 13 | tert-Butyl 5-(N-hydroxyethanimidoyl)-2,3-dihydro-1H-indole-1-carboxylate | ES/MS (m/z): 277.0 (M + H) |
| 14 | tert-Butyl 5-(N-hydroxypropanimidoyl)-2,3-dihydro-1H-indole-1-carboxylate | ES/MS (m/z): 291.0 (M + H) |

Prepare the following compounds essentially analogous to Preparation 3.

| Prep No. | Chemical Name | Physical data |
|---|---|---|
| 15 | Racemic tert-butyl 5-[1-aminoethyl]-2,3-dihydro-1H-indole-1-carboxylate | ES/MS (m/z): 246.0 (M − NH2)$^+$ |
| 16 | Racemic tert-butyl 5-[1-aminopropyl]-2,3-dihydro-1H-indole-1-carboxylate | ES/MS (m/z): 260.1 (M − NH2)$^+$ |

Preparation 17A and B

Separation of tert-butyl 5-[1-aminopropyl]-2,3-dihydro-1H-indole-1-carboxylate, Isomer 1 and tert-butyl 5-[1-aminopropyl]-2,3-dihydro-1H-indole-1-carboxylate, Isomer 2 (for chiral separation)

Purify racemic tert-butyl 5-[1-aminopropyl]-2,3-dihydro-1H-indole-1-carboxylate (Preparation 16) by chiral chromatography to afford the first eluting enantiomer (Isomer 1). MS (m/z): 260.0 (M−NH2)$^+$. Purification conditions: CHIRALPAK® AD, 8×33.5 cm column; Mobile phase: 100% MeOH (containing 0.2% N,N-dimethylethylamine); Flow rate: 400 mL/minute; UVW: 240 nm. Confirm enantiomeric enrichment of Isomer 1 by chiral analytical HPLC (>99% ee, $R_t$: 9.2 minutes; Column: CHIRALPAK® AD-H, 4.6×150 mm; Mobile phase: 100% MeOH (containing 0.2% N,N-dimethylethylamine); Flow rate: 0.6 mL/minute; UVW: 280 nm).

The above purification also yields the second eluting enantiomer (Isomer 2). ES/MS (m/z): 260.0 (M−NH2)$^+$. Confirm enantiomeric enrichment of Isomer 2 by chiral analytical HPLC (99% ee, $R_t$: 14.7 minutes; Column: CHIRALPAK® AD-H, 4.6×150 mm; Mobile phase: 100% MeOH (containing 0.2% N,N-dimethylethylamine); Flow rate: 0.6 mL/minute; UVW: 280 nm).

Preparation 18

Synthesis of racemic tert-butyl 5-{1-[(4-fluorobenzoyl)amino]ethyl}-2,3-dihydro-1H-indole-1-carboxylate Treat a solution of racemic tert-butyl 5-[1-aminoethyl]-2,3-dihydro-1H-indole-1-carboxylate (Preparation 15) (3.00 g, 11.4 mmol) in DCM (57 mL) with N,N-diisopropylethylamine (4.0 mL, 57.2 mmol). Add 4-fluorobenzoyl chloride (1.52 mL, 12.6 mmol) and stir overnight. Quench the reaction mixture with water and add saturated aqueous sodium bicarbonate solution. Separate the layers and extract twice with DCM. Dry the combined organic layers over anhydrous sodium sulfate, filter and concentrate the filtrate. Purify by silica gel column chromatography with 50-75% (10% acetone in DCM) in hexanes to give the title compound (4.29 g, 98%) as a pale yellow solid. ES/MS (m/z): 407.0 (M+Na)$^+$, 383.0 (M−H)$^-$.

Prepare the following compound essentially analogous to Preparation 18.

| Prep No. | Chemical Name | Physical data |
|---|---|---|
| 19 | Racemic tert-butyl 5-{1-[(4-fluorobenzoyl)amino]propyl}-2,3-dihydro-1H-indole-1-carboxylate | ES/MS (m/z): 421.0 (M + Na)$^+$, 397.2 (M − H)$^-$ |

Preparation 20

Synthesis of tert-butyl 5-[1-{[(benzyloxy)carbonyl]amino}propyl]-2,3-dihydro-1H-indole-1-carboxylate, Isomer A Treat a solution of tert-butyl 5-[1-aminopropyl]-2,3-dihydro-1H-indole-1-carboxylate, Isomer 2 (Preparation 17B) (3.25 g, 11.8 mmol) in DCM (47.0 mL) at room temperature with N,N-diisopropylethylamine (4.53 mL, 25.9 mmol). Add benzyl chloroformate (2.12 mL, 14.1 mmol) and stir overnight. Treat the reaction mixture with additional N,N-diisopropylethylamine (2.06 mL, 11.8 mmol) and benzyl chloroformate (0.707 mL, 4.70 mmol). Stir for 30 minutes. Quench the reaction mixture with water and add saturated aqueous sodium bicarbonate solution. Separate the layers and extract the aqueous layer twice with DCM. Dry the combined organic layers over anhydrous sodium sulfate, filter and concentrate the filtrate. Purify by silica gel column chromatography eluting with a gradient of 5-35% acetone in hexanes to give the title compound (4.47 g, 93%) as a white foam. ES/MS (m/z): 433.2 (M+Na)$^+$, 409.0 (M−H)$^-$.

Preparation 21

Synthesis of racemic N-[1-(2,3-dihydro-1H-indol-5-yl)ethyl]-4-fluorobenzamide

Add 4M hydrochloric acid in 1,4-dioxane (27.9 mL, 112 mmol) to a mixture of racemic tert-butyl 5-{1-[(4-fluorobenzoyl)amino]ethyl}-2,3-dihydro-1H-indole-1-carboxylate (Preparation 18) (4.29 g, 11.2 mmol) in DCM (112 mL). Heat the resulting mixture at 40° C. for six hours. Neutralize with 2N aqueous NaOH solution. Add 4:1 CHCl$_3$:IPA to dissolve gummy solids and separate the layers. Wash the organic layer with brine, dry over anhydrous sodium sulfate, filter and concentrate the filtrate. Purify by silica gel column chromatography eluting with a gradient of 30-60% (25% acetone in DCM) in hexanes to give the title compound (2.48 g, 78%) as a slightly off-white foam. ES/MS (m/z): 285.0 (M+H).

Prepare the following compounds essentially analogous to Preparation 21.

| Prep No. | Chemical Name | Physical data |
|---|---|---|
| 22 | Racemic N-[1-(2,3-Dihydro-1H-indol-5-yl)propyl]-4-fluorobenzamide | ES/MS (m/z): 299.0 (M + H) |
| 23 | Benzyl [1-(2,3-dihydro-1H-indol-5-yl)propyl]carbamate, Isomer A | ES/MS (m/z): 311.2 (M + H) |

Preparation 24A and B

Separation of N-[1-(2,3-dihydro-1H-indol-5-yl) ethyl]-4-fluorobenzamide, Isomer 1 and N-[1-(2,3-dihydro-1H-indol-5-yl)ethyl]-4-fluorobenzamide, Isomer 2 (for chiral separation)

Purify racemic N-[1-(2,3-dihydro-1H-indol-5-yl)ethyl]-4-fluorobenzamide (Preparation 21) by chiral SFC to afford the first eluting enantiomer (Isomer 1). ES/MS (m/z): 285.0 (M+H). Purification conditions: CHIRALPAK® AS-H, 5×15 cm column; Mobile phase: 15% iPrOH in $CO_2$; Column temperature: 40° C.; Flow rate: 300 g/minute; UVW: 250 nm. Confirm enantiomeric enrichment of Isomer 1 by chiral analytical SFC (>99% ee, $R_t$: 1.47 minutes; Column: CHIRALPAK® AS-H, 4.6×150 mm; Mobile phase: 25% iPrOH in $CO_2$; Flow rate: 5 mL/minute; UVW: 300 nm).

The above purification also yields the second eluting enantiomer (Isomer 2). ES/MS (m/z): 285.0 (M+H). Confirm enantiomeric enrichment of Isomer 2 by chiral analytical SFC (98.5% ee, $R_t$: 2.08 minutes; Column: CHIRALPAK® AS-H, 4.6×150 mm; Mobile phase: 25% iPrOH in $CO_2$; Flow rate: 5 mL/minute; UVW 300 nm).

Preparation 25

Synthesis of {5-[1-aminopropyl]-2,3-dihydro-1H-indol-1-yl}(tetrahydro-2H-pyran-4-yl)methanone, Isomer A Add a solution of benzyl{1-[1-(tetrahydro-2H-pyran-4-ylcarbonyl)-2,3-dihydro-1H-indol-5-yl]propyl}carbamate, Isomer A (Preparation 9) (2.12 g, 5.02 mmol) in EtOH (35 mL) to a nitrogen purged suspension of 20% palladium hydroxide on carbon (2.12 g) in EtOH (35 mL) in a PARR® shaker bottle. Seal, purge with nitrogen and then hydrogen. Shake under an atmosphere of hydrogen at 414 kPa (60 psi) for 3.6 hours at room temperature. Filter the reaction mixture through diatomaceous earth and concentrate the filtrate to give the title compound (1.36 g, 94%) as a grayish-white solid. ES/MS (m/z): 289.2 (M+H), 272.0 (M−NH2)$^+$.

Preparation 26

Synthesis of methyl 2-methyl-2-[1-(tetrahydro-2H-pyran-4-ylcarbonyl)-2,3-dihydro-1H-indol-5-yl]propanoate Add n-butyllithium (3.6 mL, 8.9 mmol, 2.2 M in hexanes) to a stirred 0° C. solution of dicyclohexylamine (1.9 mL, 9.6 mmol) in toluene (25 mL) under nitrogen and stir for 20 minutes. Add a solution of methyl isobutyrate (0.83 g, 8.2 mmol) in toluene (5 mL) dropwise to the previously prepared mixture and stir for 30 minutes at 0° C. Add [5-bromo-2,3-dihydro-1H-indol-1-yl](tetrahydro-2H-pyran-4-yl) methanone (Preparation 8) (2.3 g, 7.4 mmol) and degas the resulting mixture with nitrogen. Add di-µ-bromobis(tri-t-butylphosphine)dipalladium(I) (50 mg, 0.06 mmol) and allow the resulting mixture to warm to room temperature under nitrogen. After two hours, add a second portion of di-µ-bromobis(tri-t-butylphosphine)dipalladium(I) (50 mg, 0.06 mmol) and stir at room temperature under nitrogen overnight. Dilute with EtOAc and aqueous 1N HCl solution and stir for 10 minutes. Filter and rinse the solids with EtOAc. Separate the filtrate layers and wash the organic layer with saturated aqueous sodium bicarbonate solution and brine. Dry the organic layer over anhydrous sodium sulfate, filter and concentrate the filtrate. Purify by silica gel column chromatography with 20-60% EtOAc in hexanes to give the title compound (2.3 g, 94% yield, 89% purity) as a white solid. ES/MS (m/z): 332.2 (M+H).

Preparation 27

Synthesis of 2-methyl-2-[1-(tetrahydro-2H-pyran-4-ylcarbonyl)-2,3-dihydro-1H-indol-5-yl]propanoic acid Dissolve methyl 2-methyl-2-[1-(tetrahydro-2H-pyran-4-ylcarbonyl)-2,3-dihydro-1H-indol-5-yl]propanoate (Preparation 26) (2.2 g, 6.6 mmol) in THF (66 mL) and add potassium trimethylsilanolate (1.1 g, 8.6 mmol). Stir at room temperature for four days. Filter the solids and wash with THF. Dissolve the solids in water and acidify with aqueous 5N HCl solution. Cool in a refrigerator for 30 minutes. Filter to collect the title compound (1.20 g, 57%) as a white solid. ES/MS (m/z): 318.0 (M+H).

Preparation 28

Synthesis of 2-methyl-2-[1-(tetrahydro-2H-pyran-4-ylcarbonyl)-2,3-dihydro-1H-indol-5-yl]propanamide Add 1,1'-carbonyldiimidazole (126 mg, 0.763 mmol) to a stirred solution of 2-methyl-2-[1-(tetrahydro-2H-pyran-4-ylcarbonyl)-2,3-dihydro-1H-indol-5-yl]propanoic acid (Preparation 27) (202 mg, 0.636 mmol) in DCM (6.4 mL) and stir at room temperature under nitrogen for 45 minutes. Add ammonium hydroxide (1 mL, 9.55 mmol, 25% w/v in water) and stir at room temperature under nitrogen for 90 minutes. Add DMF (3 mL) to aid solubility and continue stirring at room temperature for two hours. Concentrate and purify by silica gel column chromatography with 0-10% EtOH in DCM to obtain the title compound (180 mg, 89%) as a white solid. ES/MS (m/z): 317.0 (M+H).

Preparation 29

Synthesis of [5-(1-amino-1-methylethyl)-2,3-dihydro-1H-indol-1-yl](tetrahydropyran-4-yl)methanone Add [bis(trifluoroacetoxy)iodo]benzene (115 mg, 0.26 mmol) to a stirred mixture of 2-methyl-2-[1-(tetrahydro-2H-pyran-4-ylcarbonyl)-2,3-dihydro-1H-indol-5-yl]propanamide (Preparation 28) (81 mg, 0.26 mmol) in ACN (0.25 mL) and water (0.25 mL) and stir at room temperature under nitrogen overnight. Concentrate to obtain the title compound (140 mg, 94%, 50% pure material) as a light pink solid. ES/MS (m/z): 289.2 (M+H), 272.0 (M−NH2)$^+$.

Preparation 30

Synthesis of methyl 4-fluoro-2-[(2-hydroxyethyl)amino]benzoate

Heat a mixture of methyl-2-amino-4-fluorobenzoate (2.81 g, 15.9 mmol) and 2-iodoethanol (0.879 mL, 11.2 mmol) to 90° C. for six hours then cool to room temperature. Dissolve the neat mixture in EtOAc, wash three times with aqueous 1N NaOH solution, followed by brine. Dry the organic layer over anhydrous magnesium sulfate, filter and concentrate the filtrate to obtain 2.94 g of light brown oil. Add 2-iodoethanol (1.26 mL, 15.9 mmol) and heat the mixture at 100° C. overnight. Add additional 2-iodoethanol (0.314 mL, 3.99 mmol) and continue heating at 100° C. for two hours. Cool to room temperature. Dissolve the neat mixture in EtOAc, wash three times with aqueous 1N NaOH solution, followed by brine. Dry the organic layer over anhydrous magnesium sulfate, filter and concentrate the filtrate to obtain 2.50 g brown solids. Purify by silica gel column chromatography with 20-40% EtOAc in hexanes to give the title compound (1.12 g, 33%) as a white solid. ES/MS (m/z): 214.0 (M+H).

Preparation 31

Synthesis of 4-fluoro-2-[(2-hydroxyethyl)amino]benzoic acid

Add sodium hydroxide (0.49 mL, 2.4 mmol, 5M in water) to a stirred solution of methyl 4-fluoro-2-[(2-hydroxyethyl)amino]benzoate (Preparation 30) (104 mg, 0.488 mmol) in 1,4-dioxane (2.4 mL). Stir capped at room temperature for 30 minutes then heat to 70° C. for two hours. Concentrate and acidify to approximately pH 1-2 with aqueous 1N HCl, extract twice with DCM. Dry combined organic layer over anhydrous magnesium sulfate, filter and concentrate the filtrate to obtain the title compound (89 mg, 92%) as tan solids. ES/MS (m/z): 200.0 (M+H).

Reference Preparation 1

Synthesis of 1-(2,4-difluorophenyl)-3-(2,3-dihydro-1H-indol-5-ylmethyl)urea

Stir a mixture of tert-butyl 5-(aminomethyl)indoline-1-carboxylate (4.1 g, 17 mmol) and 2,4-difluoro-1-isocyanatobenzene (3 mL, 24 mmol) in DCM (100 mL) for one hour. Quench the reaction with MeOH and water and concentrate. Dissolve the residue in DCM (30 mL) and add TFA (15 mL) and allow to stand at room temperature for two hours. Concentrate and add saturated aqueous sodium bicarbonate. Extract the mixture with MeOH/DCM (1/5, v/v). Dry the organic layer over anhydrous magnesium sulfate, filter and concentrate the filtrate. Recrystallize from EtOH to give two crops. Combine the crops to give the title compound (3.5 g, 68%). ES/MS (m/z): 304.0 (M+H).

Reference Preparation 2

Synthesis of 1-(2,4-difluorophenyl)-3-{[1-(3,4,5-tribromobenzoyl)-2,3-dihydro-1H-indol-5-yl]methyl}urea Degas (N$_2$) a solution of 1-(2,4-difluorophenyl)-3-(2,3-dihydro-1H-indol-5-ylmethyl)urea (Reference Preparation 1) (70 mg, 0.23 mmol), 3,4,5-tribromobenzoic acid (170 mg, 0.24 mmol) and 1-[bis(dimethylamino)methylene]-1H-1,2,3-triazolo[4,5-b]pyridinium 3-oxid hexafluorophosphate (134 mg, 0.35 mmol) in DMF (2 mL). Add TEA (0.08 mL, 0.6 mmol) and stir at room temperature for one hour. Directly purify the reaction mixture by reverse phase purification (Column: Redisep Rf Gold High Performance C18 Reverse Phase Column; eluent: A: 10 mM ammonium bicarbonate in water with 5% MeOH (pH 10), B: ACN; gradient: 40% B for 5 minutes then 40-95% B over 15 minutes; flow 60 mL/minute, UVW 219/254 nM) and isolate the product by lyophilization to give the title compound (149 mg, 54%). ES/MS (m/z, $^{79}$Br/$^{81}$Br): 644.0/646.0 (M+H).

EXAMPLE 1

Racemic 4-fluoro-N-{1-[1-(tetrahydro-2H-pyran-4-ylcarbonyl)-2,3-dihydro-1H-indol-5-yl]ethyl}benzamide

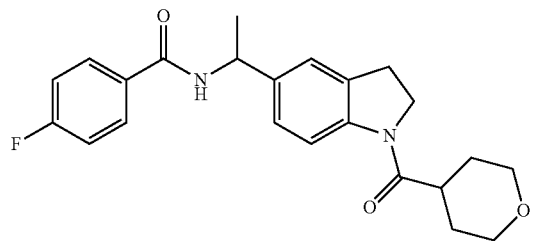

Combine racemic [5-(1-aminoethyl)-2,3-dihydro-1H-indol-1-yl](tetrahydro-2H-pyran-4-yl)methanone (Preparation 3) (420 mg, 1.53 mmol) and 4-fluorobenzoic acid (257 mg, 1.84 mmol) in DCM (15 mL). To the stirring solution add N,N-diisopropylethylamine (534 µL, 3.06 mmol) and 1-[bis(dimethylamino)methylene]-1H-1,2,3-triazolo[4,5-b]pyridinium-3-oxid hexafluorophosphate (890 mg, 2.30 mmol). Stir the resulting mixture at room temperature for 16 hours. Evaporate the solvent and purify by reverse phase column chromatography (Redisep Rf Gold High Performance C18 Reverse Phase Column, 25-100% ACN in 10 mM aqueous ammonium bicarbonate) to give the title compound (372 mg, 61%). ES/MS (m/z): 397.2 (M+H). $^1$H NMR (d$_6$-DMSO) δ 8.73 (d, J=8 Hz, 1H), 7.98 (d, J=8 Hz, 1H), 7.93-7.89 (m, 2H), 7.28-7.23 (m, 2H), 7.22 (s, 1H), 7.12 (d, J=8 Hz, 1H), 5.07 (quin, J=8 Hz, 1H), 4.14 (t, J=8 Hz, 2H), 3.85 (m, 2H), 3.36 (m, 2H), 3.09 (t, J=8 Hz, 2H), 2.80 (m, 1H), 1.57-1.66 (m, 4H), 1.41 (d, J=7 Hz, 3H).

EXAMPLE 1A

4-Fluoro-N-{(1R)-1-[1-(tetrahydro-2H-pyran-4-ylcarbonyl)-2,3-dihydro-1H-indol-5-yl]ethyl}benzamide Synthetic Method 1:

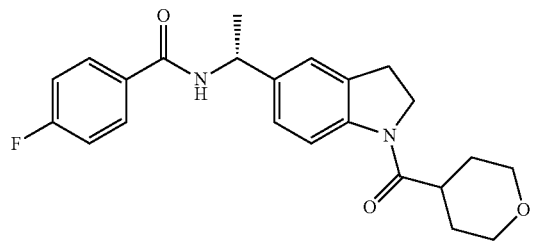

Purify racemic 4-fluoro-N-{1-[1-(tetrahydro-2H-pyran-4-ylcarbonyl)-2,3-dihydro-1H-indol-5-yl]ethyl}benzamide (Example 1) by chiral SFC to afford the first eluting enantiomer as the title compound. ES/MS (m/z): 397.0 (M+H). Purification conditions: CHIRALPAK® AD-H, 21×150 mm; Mobile phase: 40% MeOH in $CO_2$; Column temperature: 40° C.; Flow rate: 70 g/minute; UVW: 225 nm. Confirm enantiomeric enrichment of Isomer 1 by chiral analytical SFC (>99% ee, $R_t$: 1.72 minutes; Column: CHIRALPAK® AD-H, 4.6×150 mm; Mobile phase: 40% MeOH in $CO_2$; Flow rate: 5 mL/minute; UVW: 225 nm). $^1$H NMR (d6-DMSO) δ 8.73 (d, J=8 Hz, 1H), 7.98 (d, J=8 Hz, 1H), 7.93-7.89 (m, 2H), 7.28-7.23 (m, 2H), 7.22 (s, 1H), 7.12 (d, J=8 Hz, 1H), 5.07 (quin, J=8 Hz, 1H), 4.14 (t, J=8 Hz, 2H), 3.85 (m, 2H), 3.36 (m, 2H), 3.09 (t, J=8 Hz, 2H), 2.80 (m, 1H), 1.57-1.66 (m, 4H), 1.41 (d, J=7 Hz, 3H).

Synthetic Method 2:

Add TEA (9.8 mL, 70.3 mmol) and then 4-fluorobenzoyl chloride (5.85 g, 36.9 mmol) to a solution of [5-(1-aminoethyl)-2,3-dihydro-1H-indol-1-yl](tetrahydro-2H-pyran-4-yl)methanone, Isomer 1 (Preparation 4A) (9.65 g, 35.2 mmol) in DCM (176 mL) at 0° C. Allow the resulting mixture to warm to room temperature and stir overnight. Dilute the reaction mixture with EtOAc (300 mL), filter through a silica gel pad and wash with EtOAc. Concentrate the filtrate and purify by silica gel column chromatography with a gradient from 25-30% ACN in DCM to give the title compound (9.4 g, 67.1%) as an off-white solid. MS (m/z): 397.2 (M+H). Confirm enantiomeric enrichment by chiral analytical SFC (>99% ee, $R_t$: 1.74 minutes; Column: CHIRALPAK® AD-H, 4.6×150 mm; Mobile phase: 40% MeOH in $CO_2$; Flow rate: 5 mL/minute; UVW: 225 nm). $^1$H NMR (d6-DMSO) δ 8.73 (d, J=8 Hz, 1H), 7.98 (d, J=8 Hz, 1H), 7.93-7.89 (m, 2H), 7.28-7.23 (m, 2H), 7.22 (s, 1H), 7.12 (d, J=8 Hz, 1H), 5.07 (quin, J=8 Hz, 1H), 4.14 (t, J=8 Hz, 2H), 3.85 (m, 2H), 3.36 (m, 2H), 3.09 (t, J=8 Hz, 2H), 2.80 (m, 1H), 1.57-1.66 (m, 4H), 1.41 (d, J=7 Hz, 3H).

Synthetic Method 3:

Add TEA (65 mL, 468 mmol) to a mixture of [5-(1-aminoethyl)-2,3-dihydro-1H-indol-1-yl](tetrahydro-2H-pyran-4-yl)methanone hydrochloride, Isomer 1 (Preparation 7B) (70 g, 225 mmol) in DCM (700 mL) at 0-5° C. Add 4-fluorobenzoyl chloride (37.85 g, 239 mmol) dropwise. Warm the mixture to room temperature and stir for two hours. Add water dropwise at a rate to keep the temperature below 30° C. and stir the mixture at 20-30° C. for one hour. Separate the layers and wash the organic layer with 18% aqueous $H_2SO_4$. Separate the layers and wash the organic layer with 7% aqueous $NaHCO_3$. Separate the layers and wash the organic layer with water. Separate the layers and then pass the organic solution through a carbon filter. Treat the solution with SI-Thiol (7 g) and heat the mixture to 40° C. Stir the resulting mixture for 12 hours. Cool the mixture to room temperature and filter the mixture through diatomateous earth. Concentrate the organic layer to 200 mL (~3 vols). Add acetone (140 mL, 2 vols) and concentrate the resulting mixture to 200 mL (~3 vols). Treat with additional acetone (280 mL, 4 vols) and water (280 mL, 4 vols). Heat at 65° C. for two hours until reaction is a clear solution. Cool slowly to 30° C. over three hours. Stir at 30° C. for one hour. Add water (140 mL, 2 vols) dropwise and continue stirring at 30° C. for one hour. Cool slowly to 3-8° C. over approximately two hours. Stir at this temperature for six hours. Filter and rinse the solids with water (140 mL, 2 vols). Dry the solids at 55° C. for four to six hours. Obtain the desired product as a white solid (55 g, 61.6%).

X-Ray Powder Diffraction Collection Procedure for Example 1A

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. Collect the crystal form diffraction patterns at ambient temperature and relative humidity.

X-Ray Powder Diffraction Collection Procedure for 1A Method 3

A prepared sample of Example 1A (Synthetic method 3) is characterized by an XRD pattern using CuKa radiation as having diffraction peaks (2-theta values) as described in Table 1 below. Specifically the pattern contains a peak at 17.38° in combination with one or more of the peaks selected from the group consisting of 12.51°, 15.65°, 16.37°, 17.56°, 21.48° and 25.23° with a tolerance for the diffraction angles of 0.2 degrees)(2θ±0.2°.

TABLE 1

X-ray powder diffraction peaks of Example 1A method 3

| Peak | Angle (2-Theta °) | Intensity (%) |
|---|---|---|
| 1 | 9.99 | 13 |
| 2 | 12.51 | 73 |
| 3 | 15.65 | 90 |
| 4 | 16.37 | 57 |
| 5 | 17.38 | 100 |
| 6 | 17.56 | 62 |
| 7 | 18.79 | 25 |
| 8 | 19.81 | 38 |
| 9 | 21.48 | 56 |
| 10 | 23.38 | 43 |
| 11 | 24.41 | 21 |
| 12 | 24.70 | 17 |
| 13 | 25.23 | 64 |
| 14 | 25.46 | 28 |
| 15 | 27.69 | 15 |

Determination of Absolute Configuration for Example 1A

Prepare a single crystal of 4-fluoro-N-{(1R)-1-[1-(tetrahydro-2H-pyran-4-ylcarbonyl)-2,3-dihydro-1H-indol-5-yl]ethyl}benzamide by suspending 10 mg of 4-fluoro-N-{(1R)-1-[1-(tetrahydro-2H-pyran-4-ylcarbonyl)-2,3-dihydro-1H-indol-5-yl]ethyl}benzamide in 1:1 EtOH/heptane (1.75 mL) and slurrying on an orbital shaker for three days. Use a colorless bladed-like specimen of 4-fluoro-N-{(1R)-1-[1-(tetrahydro-2H-pyran-4-ylcarbonyl)-2,3-dihydro-1H-indol-5-yl]ethyl}benzamide, approximate dimensions 0.020 mm×0.080 mm×0.300 mm, for the X-ray crystallographic analysis. Measure the X-ray intensity data using an Iμ CuKα radiation source (λ=1.54178 Å) and a Bruker D8 Venture based 3-circle goniometer diffractometer equipped with Photon 100 SL area detector. Collect a total of 8840 frames.

Integrate the frames with the Bruker SAINT software package using a narrow-frame algorithm. The integration of the data using a monoclinic unit cell yielded a total of 7242 reflections to a maximum 0 angle of 68.28° (0.83 Å resolution), of which 3059 are independent (average redundancy 2.367, completeness=95.9%, Rint=5.83%, Rsig=6.58%) and 2893 (94.57%) is greater than $2\sigma(F^2)$. The final cell constants of a=5.5831(13) Å, b=5.1082(9) A, c=35.013(6) Å, β=90.578(17) °, volume=998.5(3) Å$^3$, are based upon the refinement of the XYZ-centroids of 6280 reflections above 20 σ(I) with 10.09°<2θ<136.8°. Correct the data for absorption effects using the multi-scan method (SADABS). The ratio of minimum to maximum apparent transmission is 0.784. The calculated minimum and maximum transmission coefficients (based on crystal size) are 0.8020 and 0.9850. Solve the structure and refine using the Bruker SHELXTL Software Package, using the space group P 2$_1$, with Z=2 for the formula unit, $C_{23}H_{25}FN_2O_3$. The final anisotropic full-matrix least-squares refinement on F2 with 264 variables converge at R1=9.17%, for the observed data and wR2=23.48% for all data. The goodness-of-fit is 1.141. The largest peak in the final difference electron density synthesis is 0.506 e–/Å$^3$ and the largest hole is –0.358 e–/Å$^3$ with an RMS deviation of 0.088 e–/Å$^3$. On the basis of the final model, the calculated density is 1.319 g/cm$^3$ and F(000), 420 e–. The absolute structure parameter refines to 0.12(16), verifying the stereochemistry of the chiral center. The absolute structure is determined to be the R-configuration at the stereocenter.

EXAMPLE 1B

4-Fluoro-N-{(1S)-1-[1-(tetrahydro-2H-pyran-4-ylcarbonyl)-2,3-dihydro-1H-indol-5-yl]ethyl}benzamide, Isomer 2

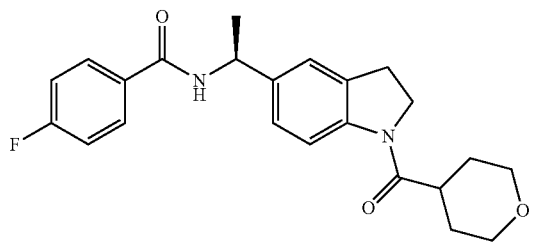 [SMILES: C[C@H](NC(=O)c1ccc(F)cc1)c1ccc2c(c1)CCN2C(=O)C1CCOCC1]

Purify racemic 4-fluoro-N-{1-[1-(tetrahydro-2H-pyran-4-ylcarbonyl)-2,3-dihydro-1H-indol-5-yl]ethyl}benzamide (Example 1) by chiral chromatography to afford the second eluting enantiomer as the title compound. ES/MS (m/z): 397.0 (M+H). Purification conditions: Column: CHIRALPAK® AD-H, 21×150 mm; Mobile phase: 40% MeOH in CO$_2$; Column temperature: 40° C.; Flow rate: 70 g/minute; UVW: 225 nm. Confirm enantiomeric enrichment of Isomer 2 by chiral analytical SFC (98.3% ee, R$_t$: 2.37 minutes; Column: CHIRALPAK® AD-H, 4.6×150 mm; Mobile phase: 40% MeOH in CO$_2$; Flow rate: 5 mL/minute; UVW: 225 nm). $^1$H NMR (d6-DMSO) δ 8.73 (d, J=8 Hz, 1H), 7.98 (d, J=8 Hz, 1H), 7.93-7.89 (m, 2H), 7.28-7.23 (m, 2H), 7.22 (s, 1H), 7.12 (d, J=8 Hz, 1H), 5.07 (quin, J=8 Hz, 1H), 4.14 (t, J=8 Hz, 2H), 3.85 (m, 2H), 3.36 (m, 2H), 3.09 (t, J=8 Hz, 2H), 2.80 (m, 1H), 1.57-1.66 (m, 4H), 1.41 (d, J=7 Hz, 3H).

Prepare Example 2 essentially analogous to Example 1, using the starting material from Preparation 3.

| Ex No. | Chemical Name | Structure | Physical data |
|---|---|---|---|
| 2 | Racemic 4-chloro-N-{1-[1-(tetrahydro-2H-pyran-4-ylcarbonyl)-2,3-dihydro-1H-indol-5-yl]ethyl}benzamide | 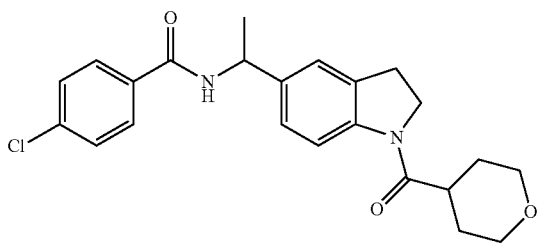 [SMILES: CC(NC(=O)c1ccc(Cl)cc1)c1ccc2c(c1)CCN2C(=O)C1CCOCC1] | ES/MS (m/z): 413.0 (M + H) |

EXAMPLE 2A AND 2B

4-Chloro-N-{1-[1-(tetrahydro-2H-pyran-4-ylcarbonyl)-2,3-dihydro-1H-indol-5-yl]ethyl}benzamide, Isomer 1 and 4-Chloro-N-{1-[1-(tetrahydro-2H-pyran-4-ylcarbonyl)-2,3-dihydro-1H-indol-5-yl]ethyl}benzamide, Isomer 2

Purify racemic 4-chloro-N-{1-[1-(tetrahydro-2H-pyran-4-ylcarbonyl)-2,3-dihydro-1H-indol-5-yl]ethyl}benzamide (Example 2) by chiral SFC to afford the first eluting enantiomer (Isomer 1). ES/MS (m/z): 413.0 (M+H). Purification conditions: CHIRALPAK® AD-H, 21×150 mm; Mobile phase: 40% iPrOH in CO$_2$; Flow rate: 70 g/minute; UVW: 260 nm. Confirm enantiomeric enrichment of Isomer 1 by chiral analytical SFC (>99% ee, R1=1.97 minutes; Column: CHIRALPAK® AD-H, 4.6×150 mm; Mobile phase: 40% iPrOH in CO$_2$; Column temperature: 40° C.; Flow rate: 5 mL/minute; UVW: 225 nm).

The above purification also yields the second eluting enantiomer (Isomer 2). ES/MS (m/z): 413.0 (M+H). Confirm enantiomeric enrichment of Isomer 2 by chiral analytical SFC (>99% ee, R$_t$: 3.04 minutes; Column: CHIRALPAK® AD-H, 4.6×150 mm; Mobile phase: 40% iPrOH in CO$_2$; Flow rate: 5 mL/minute; UVW: 225 nm).

Prepare Examples 3 through Example 9 essentially analogous to Example 1, using the starting material from Preparation 3.

| Ex No. | Chemical Name | Structure | Physical data |
|---|---|---|---|
| 3 | Racemic 4-cyano-N-{1-[1-(tetrahydro-2H-pyran-4-ylcarbonyl)-2,3-dihydro-1H-indol-5-yl]ethyl}benzamide | 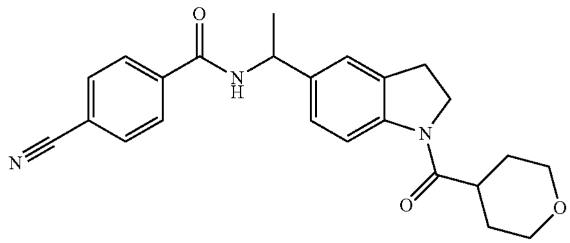 [SMILES: CC(NC(=O)c1ccc(C#N)cc1)c1ccc2c(c1)CCN2C(=O)C1CCOCC1] | ES/MS (m/z): 404.4 (M + H) |
| 4 | Racemic N-{1-[1-(tetrahydro-2H-pyran-4-ylcarbonyl)-2,3-dihydro-1H-indol-5-yl]ethyl}benzamide | 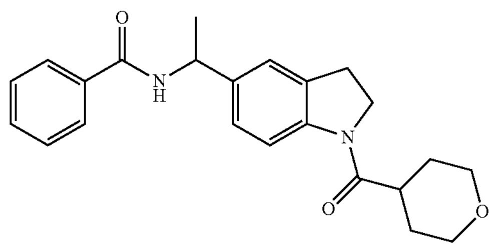 [SMILES: CC(NC(=O)c1ccccc1)c1ccc2c(c1)CCN2C(=O)C1CCOCC1] | ES/MS (m/z): 379.4 (M + H) |
| 5 | Racemic 4-methyl-N-{1-[1-(tetrahydro-2H-pyran-4-ylcarbonyl)-2,3-dihydro-1H-indol-5-yl]ethyl}benzamide | 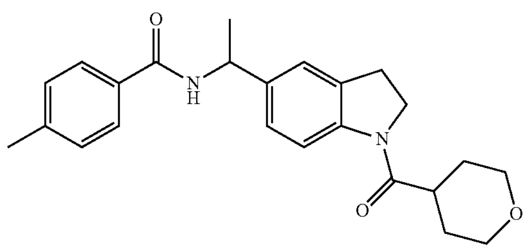 [SMILES: Cc1ccc(C(=O)NC(C)c2ccc3c(c2)CCN3C(=O)C2CCOCC2)cc1] | ES/MS (m/z): 393.4 (M + H) |
| 6 | Racemic 4-chloro-3-fluoro-N-{1-[1-(tetrahydro-2H-pyran-4-ylcarbonyl)-2,3-dihydro-1H-indol-5-yl]ethyl}benzamide | 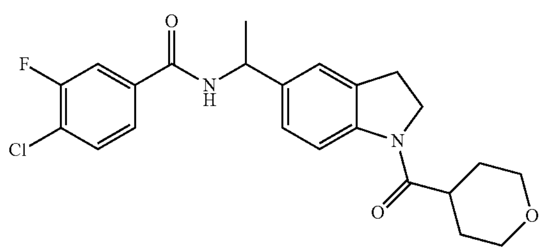 [SMILES: CC(NC(=O)c1ccc(Cl)c(F)c1)c1ccc2c(c1)CCN2C(=O)C1CCOCC1] | ES/MS (m/z): 431.4 (M + H) |
| 7 | Racemic 3-chloro-4-fluoro-N-{1-[1-(tetrahydro-2H-pyran-4-ylcarbonyl)-2,3-dihydro-1H-indol-5-yl]ethyl}benzamide | 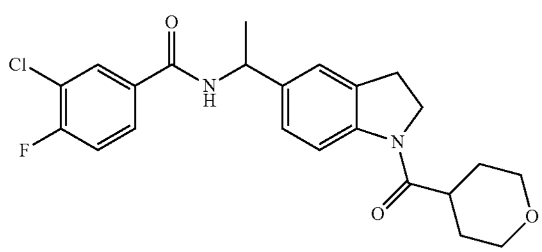 [SMILES: CC(NC(=O)c1ccc(F)c(Cl)c1)c1ccc2c(c1)CCN2C(=O)C1CCOCC1] | ES/MS (m/z): 431.4 (M + H) |
| 8 | Racemic 4-ethenyl-N-{1-[1-(tetrahydro-2H-pyran-4-ylcarbonyl)-2,3-dihydro-1H-indol-5-yl]ethyl}benzamide | 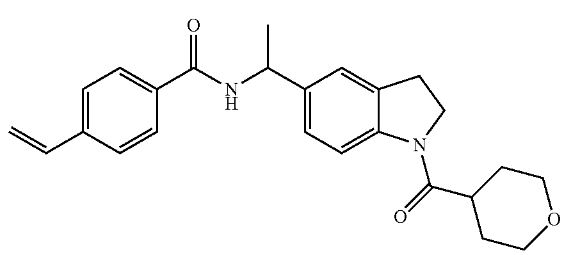 [SMILES: C=Cc1ccc(C(=O)NC(C)c2ccc3c(c2)CCN3C(=O)C2CCOCC2)cc1] | ES/MS (m/z): 405.4 (M + H) |

| Ex No. | Chemical Name | Structure | Physical data |
|---|---|---|---|
| 9 | Racemic 2,4-difluoro-N-{1-[1-(tetrahydro-2H-pyran-4-ylcarbonyl)-2,3-dihydro-1H-indol-5-yl]ethyl}benzamide | 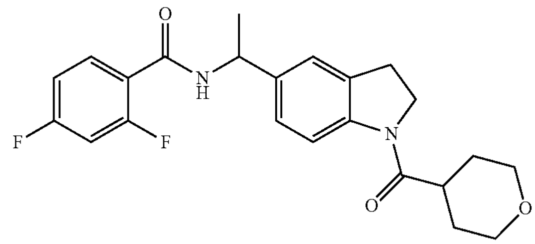 [SMILES: CC(NC(=O)c1ccc(F)cc1F)c1ccc2c(c1)CCN2C(=O)C1CCOCC1] | ES/MS (m/z): 415.0 (M + H) |

EXAMPLE 9A AND B 2,4-Difluoro-N-{1-[1-(tetrahydro-2H-pyran-4-ylcarbonyl)-2,3-dihydro-1H-indol-5-yl]ethyl}benzamide, Isomer 1 and 2,4-Difluoro-N-{1-[1-(tetrahydro-2H-pyran-4-ylcarbonyl)-2,3-dihydro-1H-indol-5-yl]ethyl}benzamide, Isomer 2

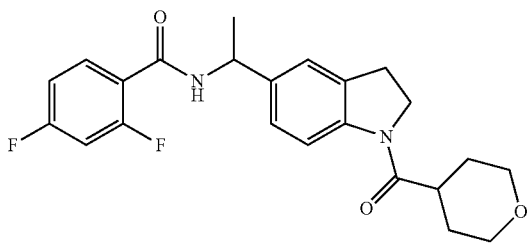 [SMILES: CC(NC(=O)c1ccc(F)cc1F)c1ccc2c(c1)CCN2C(=O)C1CCOCC1]

Purify racemic 2,4-difluoro-N-{1-[1-(tetrahydro-2H-pyran-4-ylcarbonyl)-2,3-dihydro-1H-indol-5-yl]ethyl}benzamide (Example 9) by chiral SFC to afford the first eluting enantiomer (Isomer 1). ES/MS (m/z): 415.0 (M+H). Purification conditions: CHIRALPAK® AD-H, 21×150 mm; Mobile phase: 40% MeOH in CO$_2$; Column temperature: 40° C.; Flow rate: 70 g/minute; UVW: 225 nm. Confirm enantiomeric enrichment of Isomer 1 by chiral analytical (98.6% ee, R$_t$: 1.72 minutes; Column: CHIRALPAK® AD-H, 4.6×150 mm; Mobile phase: 40% MeOH in CO$_2$; Flow rate: 5 mL/minute; UVW: 225 nm).

The above purification also yields the second eluting (Isomer 2). ES/MS (m/z): 415.2 (M+H). Confirm enantiomeric enrichment of Isomer 2 by chiral analytical SFC (98.5% ee, R$_t$: 2.60 minutes; Column: CHIRALPAK® AD-H, 4.6×150 mm; Mobile phase: 40% MeOH in CO$_2$; Flow rate: 5 mL/minute; UVW: 225 nm).

Prepare Examples 10 through Example 13 essentially analogous to Example 1, using the starting material from Preparation 7.

| Ex No. | Chemical Name | Structure | Physical data |
|---|---|---|---|
| 10 | 4-(Difluoromethyl)-N-{1-[1-(tetrahydro-2H-pyran-4-ylcarbonyl)-2,3-dihydro-1H-indol-5-yl]ethyl}benzamide, Isomer A | 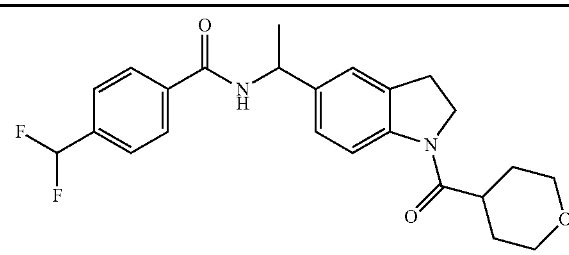 | ES/MS (m/z): 429.0 (M + H) |
| 11 | 4-(Fluoromethyl)-N-{1-[1-(tetrahydro-2H-pyran-4-ylcarbonyl)-2,3-dihydro-1H-indol-5-yl]ethyl}benzamide, Isomer A | 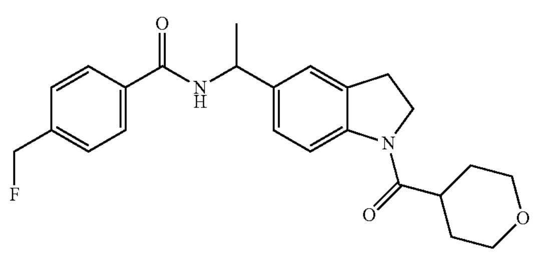 [SMILES: CC(NC(=O)c1ccc(CF)cc1)c1ccc2c(c1)CCN2C(=O)C1CCOCC1] | ES/MS (m/z): 411.2 (M + H) |
| 12 | 2-(Benzyloxy)-4-(fluoro)-N-{1-[1-(tetrahydro-2H-pyran-4-ylcarbonyl)-2,3-dihydro-1H-indol-5-yl]ethyl}benzamide, Isomer A | 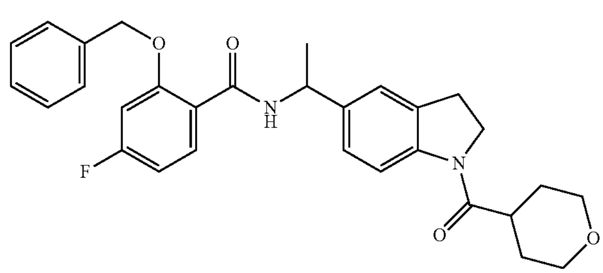 [SMILES: CC(NC(=O)c1ccc(F)cc1OCc1ccccc1)c1ccc2c(c1)CCN2C(=O)C1CCOCC1] | ES/MS (m/z): 503.2 (M + H) |

| Ex No. | Chemical Name | Structure | Physical data |
|---|---|---|---|
| 13 | 4-Fluoro-2-[(2-hydroxyethyl)amino]-N-{1-[1-(tetrahydro-2H-pyran-4-ylcarbonyl)-2,3-dihydro-1H-indol-5-yl]ethyl]benzamide, Isomer A | 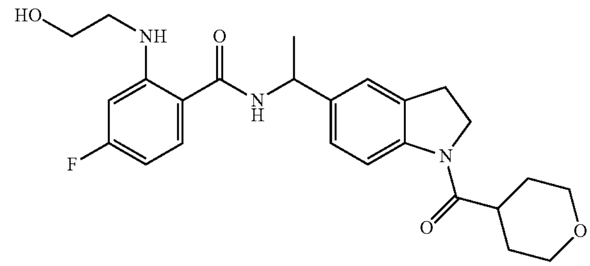 [SMILES: CC(NC(=O)c1ccc(F)cc1NCCO)c1ccc2c(c1)CCN2C(=O)C1CCOCC1] | ES/MS (m/z): 456.2 (M + H) |

Prepare Examples 14 and 15 essentially analogous to Example 1A, Synthetic method 2.

| Ex No. | Chemical Name | Structure | Physical data |
|---|---|---|---|
| 14 | 4-Fluoro-N-{2-[1-(tetrahydro-2H-pyran-4-ylcarbonyl)-2,3-dihydro-1H-indol-5-yl]propan-2-yl}benzamide | 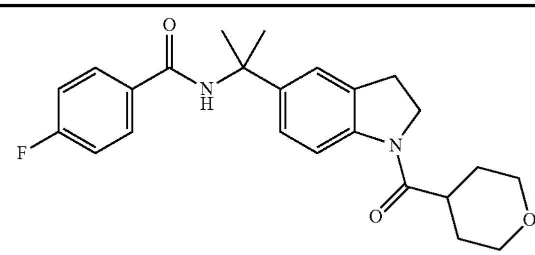 | ES/MS (m/z): 411.2 (M + H) |
| 15 | 4-Cyano-N-{1-[1-(tetrahydro-2H-pyran-4-ylcarbonyl)-2,3-dihydro-1H-indol-5-yl]propyl}benzamide, Isomer A | 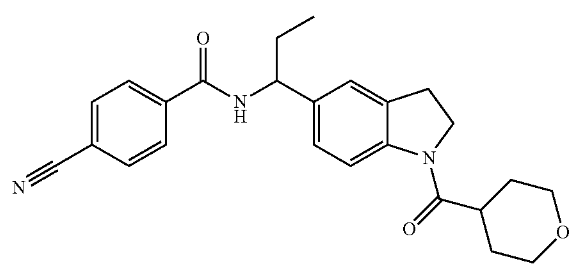 [SMILES: CCC(NC(=O)c1ccc(C#N)cc1)c1ccc2c(c1)CCN2C(=O)C1CCOCC1] | ES/MS (m/z): 418.2 (M + H) |

EXAMPLE 16

Diastereomeric 4-Fluoro-N-[1-{1-[tetrahydro-2H-pyran-3-ylcarbonyl]-2,3-dihydro-1H-indol-5-yl}ethyl]benzamide (mix of 2 diastereomers)

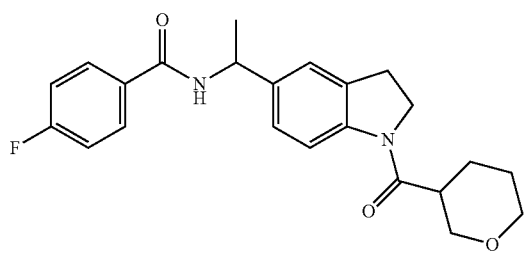 [SMILES: CC(NC(=O)c1ccc(F)cc1)c1ccc2c(c1)CCN2C(=O)C1CCCOC1]

Treat a mixture of N-[1-(2,3-dihydro-1H-indol-5-yl)ethyl]-4-fluorobenzamide, Isomer 1 (Preparation 24A) (150 mg, 0.528 mmol), racemic tetrahydropyran-3-carboxylic acid (100 mg, 0.739 mmol) and N,N-diisopropylethylamine (0.277 mL, 1.58 mmol) in DCM (5.28 mL) with 1-[bis(dimethylamino)methylene]-1H-1,2,3-triazolo[4,5-b]pyridinium-3-oxid hexafluorophosphate (304 mg, 0.791 mmol). Stir at room temperature for 45 minutes. Dilute the reaction mixture with DCM. Add water and saturated aqueous sodium bicarbonate solution. Separate the layers and extract the aqueous layer twice with DCM. Pass the combined organic layer through a hydrophobic frit (ISOLUTE® phase separator cartridge) and concentrate the filtrate. Purify by silica gel column chromatography eluting with a gradient of 20-55% acetone in hexanes to give the title compound (184 mg, 88%) as a white solid. ES/MS (m/z): 397.2 (M+H).

EXAMPLE 16A AND B

4-Fluoro-N-[1-{1-[tetrahydro-2H-pyran-3-ylcarbonyl]-2,3-dihydro-1H-indol-5-yl]ethyl}benzamide, Isomer 1 and 4-Fluoro-N-[1-{1-[tetrahydro-2H-pyran-3-ylcarbonyl]-2,3-dihydro-1H-indol-5-yl]ethyl}benzamide, Isomer 2

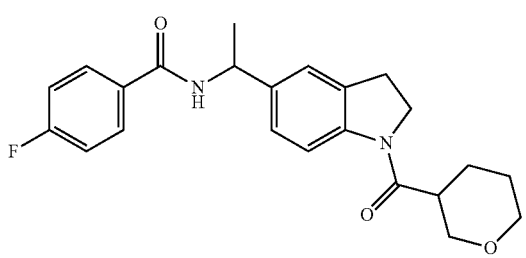

Purify diasteromeric 4-fluoro-N-[1-{1-[tetrahydro-2H-pyran-3-ylcarbonyl]-2,3-dihydro-1H-indol-5-yl}ethyl]benzamide (Example 16) by chiral chromatography to afford the first eluting diastereomer (Isomer 1). MS (m/z): 397.2 (M+H). Purification conditions: CHIRALCEL® OJ-H, 30×250 mm; Mobile phase: 100% MeOH; Flow rate: 30 mL/minute; UVW: 225 nm. Confirm enantiomeric enrichment of Isomer 1 by chiral analytical HPLC (>99% de, $R_t$: 3.42 minutes; Column: CHIRALCEL® OJ-H, 4.6×150 mm; Mobile phase: 100% MeOH (containing 0.2% isopropylamine); Flow rate: 1 mL/minute; UVW: 225 nm).

The above purification also yields the second eluting (Isomer 2). ES/MS (m/z): 397.2 (M+H). Confirm enantiomeric enrichment of Isomer 2 by chiral analytical HPLC (97.8% de, $R_t$: 4.66 minutes; Column CHIRALCEL® OJ-H, 4.6×150 mm; Mobile phase: 100% MeOH (containing 0.2% isopropylamine); Flow rate: 1 mL/minute; UVW: 225 nm).

EXAMPLE 17

4-Fluoro-2-hydroxy-N-{1-[1-(tetrahydro-2H-pyran-4-ylcarbonyl)-2,3-dihydro-1H-indol-5-yl]ethyl}benzamide, Isomer A

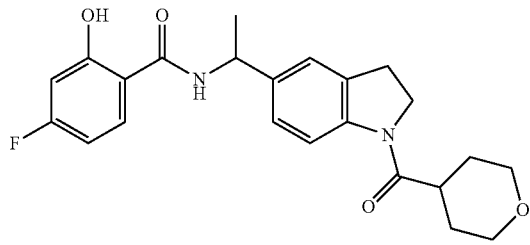 [SMILES: CC(NC(=O)c1ccc(F)cc1O)c1ccc2c(c1)CCN2C(=O)C1CCOCC1]

Add 10% Pd/C (10 mg) to a nitrogen flushed solution of 2-(benzyloxy)-4-fluoro-N-{1-[1-(tetrahydro-2H-pyran-4-ylcarbonyl)-2,3-dihydro-1H-indol-5-yl]ethyl}benzamide, Isomer A (Example 12) (96.0 mg, 0.19 mmol) in ethanol (2 mL) and hydrogenate with 1 atm (101 kPa) of hydrogen at room temperature for one hour. Filter over diatomaceous earth and concentrate the filtrate to obtain the desired compound (66 mg, 84%) as a white solid. ES/MS (m/z): 413.0 (M+H).

EXAMPLE 18

Racemic 4-fluoro-N-{1-[1-(tetrahydro-2H-pyran-4-ylcarbonyl)-2,3-dihydro-1H-indol-5-yl]propyl}benzamide

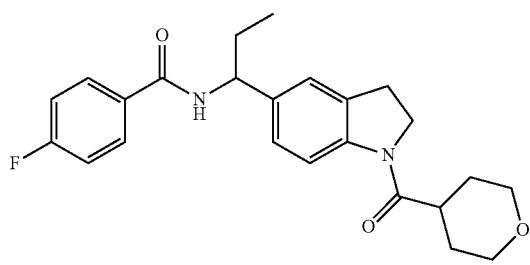 [SMILES: CCC(NC(=O)c1ccc(F)cc1)c1ccc2c(c1)CCN2C(=O)C1CCOCC1]

Treat a mixture of racemic N-[1-(2,3-dihydro-1H-indol-5-yl)propyl]-4-fluorobenzamide (Preparation 22) (200 mg, 0.650 mmol) in DCM (6.5 mL) with N,N-diisopropylethylamine (0.228 mL, 1.30 mmol). Add tetrahydropyran-4-carbonyl chloride (110 mg, 0.715 mmol) and stir for 30 minutes. Dilute the reaction mixture with DCM. Add water and saturated aqueous sodium bicarbonate solution. Separate the layers and extract the aqueous layer twice with DCM. Pass the combined organic layer through a hydrophobic frit (ISOLUTE® phase separator cartridge) and concentrate the filtrate. Purify by silica gel column chromatography eluting with a gradient of 20-60% acetone in hexanes to give the title compound as a light peach-colored foam (244 mg, 91%). ES/MS (m/z): 411.2 (M+H).

EXAMPLE 18A AND B

4-Fluoro-N-{1-[1-(tetrahydro-2H-pyran-4-ylcarbonyl)-2,3-dihydro-1H-indol-5-yl]propyl}benzamide, Isomer 1 and 4-Fluoro-N-{1-[1-(tetrahydro-2H-pyran-4-ylcarbonyl)-2,3-dihydro-1H-indol-5-yl]propyl}benzamide, Isomer 2

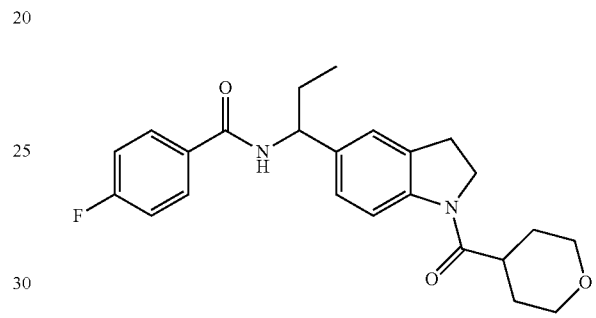

Purify racemic 4-fluoro-N-{1-[1-(tetrahydro-2H-pyran-4-ylcarbonyl)-2,3-dihydro-1H-indol-5-yl]propyl}benzamide (Example 18) by chiral SFC chromatography to afford the first eluting enantiomer (Isomer 1). ES/MS (m/z): 411.2 (M+H). Purification conditions: CHIRALPAK® AS-H, 21×150 mm column; Mobile phase: 25% MeOH in $CO_2$; Column temperature: 40° C.; Flow rate: 80 g/minute; UVW: 260 nm. Confirm enantiomeric enrichment of Isomer 1 by chiral analytical SFC (>99% ee, $R_t$: 0.92 minutes; Column: CHIRALPAK® AS-H, 4.6×150 mm; Mobile phase: 25% MeOH in $CO_2$; Flow rate: 5 mL/minute; UVW: 225 nm).

The above purification also yields the second eluting enantiomer (Isomer 2). ES/MS (m/z): 411.2 (M+H). Confirm enantiomeric enrichment of Isomer 2 by chiral analytical SFC (>99% ee, $R_t$: 1.53 minutes; Column: CHIRALPAK® AS-H, 4.6×150 mm; Mobile phase: 25% MeOH in $CO_2$; Flow rate: 5 mL/minute; UVW: 225 nm).

REFERENCE EXAMPLE 1

1-(2,4-Difluorophenyl)-3-{[1-(3,4,5-tritritiobenzoyl)-2,3-dihydro-1H-indol-5-yl]methyl}urea

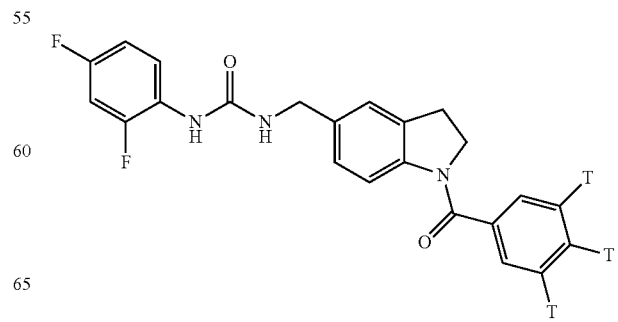

In a tritiation flask, stir 1-(2,4-difluorophenyl)-3-{[1-(3,4,5-tribromobenzoyl)-2,3-dihydro-1H-indol-5-yl]methyl}urea (3 mg, 0.005 mmol), palladium (10% on carbon, 3 mg) and N,N-diisopropylethylamine (10 µL, 0.06 mmol) in DMF (1 mL) under 3Ci of tritium for three hours. Filter the reaction and co-evaporate the filtrate with EtOH to remove the labile tritium. Dissolve the residue in EtOH and purify by reverse phase column chromatography (Column: GEMINI® C18 250×10 mm; Mobile phase: A: water/TFA (1000:1), B: ACN/TFA (1000:1); gradient: 20-70% B over 60 minutes; flowrate 3 mL/minute) to give the title compound which was dissolved in EtOH. MS: 414.19 (M+H) and 74 Ci/mmol.

REFERENCE EXAMPLE 2

1-(2,4-Difluorophenyl)-3-{[1-(phenylcarbonyl)-2,3-dihydro-1H-indol-5-yl]methyl}urea

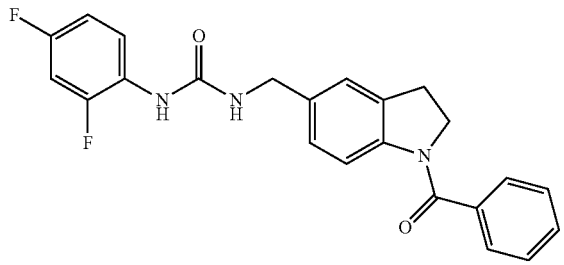 [SMILES: O=C(NCc1ccc2c(c1)CCN2C(=O)c1ccccc1)Nc1ccc(F)cc1F]

Dissolve 1-(2,4-difluorophenyl)-3-(2,3-dihydro-1H-indol-5-ylmethyl)urea (300 mg, 0.99 mmol) in DCM (20 mL) and add benzoyl chloride (0.13 mL, 1.1 mmol) and TEA (0.27 mL, 1.9 mmol). Stir the reaction mixture at room temperature for two hours. Concentrate and purify the residue by reverse phase purification (Column: Redisep Rf Gold High Performance C18 Reverse Phase Column; Mobile phase: A: 0.1% formic acid in water, B: ACN; gradient: 0-80% B over 30 minutes; flow rate: 60 mL/minute, UVW: 219/254 nm) and isolate the product by lyophilization to give the title compound (403 mg, 79%). ES/MS (m/z): 408.2 (M+H).

The immune system is a critical checkpoint that restrains tumor development. As such, cancers have evolved many mechanisms to evade, suppress, or otherwise subvert the immune system. While tryptophan is absolutely essential for cancer cell growth, its degradation is selected for in a broad array of cancers through the expression of indoleamine 2,3 dioxygenase (IDO1) either by the cancer cell itself (intrinsic), or by cells in the microenvironment or tumor draining lymph nodes (TDLNs) (extrinsic). The selective activation of IDO1 in the tumor microenvironment while counter to rapid cell growth provides the tumor with an effective strategy to avoid immunosurveillance, a critical checkpoint in cancer development and resistance to therapy. The immunosuppressive activity of IDO1 is a direct result of the local depletion of tryptophan and the concomitant production of kynurenine, both of which are immunosuppressive.

The immunosuppressive role of IDO1 activity impacts multiple cell types including cell suppression [T-cells (Frumento, et al. (2002) J Exp Med 196(4): 459-468; Terness, et al. (2002) J Exp Med 196(4): 447-457) and NK cells (Della Chiesa, et al. (2006) Blood 108(13): 4118-4125)], cell development [regulatory T-cells (Sharma, et al. (2007) J Clin Invest 117(9): 2570-2582; Chen, et al. (2008) J Immunol 181(8): 5396-5404; Baban, et al. (2009) J Immunol 183(4): 2475-2483)] and suppressive antigen presenting cells [suppressive dendritic cells and macrophages (Munn, et al. (2004) J Clin Invest 114(2): 280-290; Munn, et al. (2005) Immunity 22(5): 633-642; Sharma, et al. (2007) J Clin Invest 117(9): 2570-2582)], and recruitment and expansion [myeloid-derived suppressor cells (Yu, et al. (2014) J Immunol 193(5): 2574-2586; Holmgaard, et al. (2015) Cell Rep 13(2): 412-424)]. IDO1 activity exhibits these effects through depletion of tryptophan and the concomitant increase in kynurenine in the tumor, the tumor microenvironment and TDLNs.

Both the local depletion of tryptophan and the production of kynurenine by IDO1 expression in the tumor microenvironment or in TDLNs support the development and activation of Tregs (Sharma, et al. (2007) J Clin Invest 117(9): 2570-2582), MDSCs (Holmgaard, et al. (2015) Cell Rep 13(2): 412-424), and regulatory dendritic cells (Sharma, et al. (2007) J Clin Invest 117(9): 2570-2582) all of which play immunosuppressive roles that support tumor growth. The depletion of tryptophan supports Treg development through the activation of the stress response kinase GCN2, which is stimulated in response to the accumulation of uncharged tRNAs. T-cells lacking GCN2 are not susceptible to IDO1-mediated inhibition of proliferation or the induction of an anergic phenotype (Munn, et al. (2005) Immunity 22(5): 633-642). In addition to tryptophan depletion, IDO1 activity leads to high concentrations of the downstream metabolite kynurenine, an important immunosuppressive molecule. Similar to tryptophan depletion, the activation of aryl hydrocarbon receptor (AHR) by kynurenine is essential for the generation of regulatory T-cells (Mezrich, et al. (2010) J Immunol 185(6): 3190-3198), and elevated production of kynurenine and expression of AHR correlate with poor prognosis in human brain cancer (Opitz, et al. (2011) Nature 478(7368): 197-203). Kynurenine blocks T-cell and NK cell proliferation (Boyland, et al. (1956) Biochem J 64(3): 578-582) and is an agonist of the AHR receptor (Mezrich, et al. (2010) J Immunol 185(6): 3190-3198; Opitz, et al. (2011) Nature 478(7368): 197-203), a transcription factor that regulates innate immune-mediated production of cytokines such as IL-1β, IL-6 and IL-21, and is overexpressed in several cancers where it is thought to facilitate tumor progression and resistance to therapy (Julliard, et al. (2014) Front Immunol 5: 458). In fact, the intrinsic expression of IDO1 in cancer is regulated, in part, by kynurenine-mediated activation of an AHR-IL-6-STATS signaling loop that enforces the expression of IDO1 and inhibits T-cell proliferation. Expression of this IDO1 signaling axis is associated with a reduction in relapse free survival in lung cancer patients (Litzenburger, et al. (2014) Oncotarget 5(4): 1038-1051). IDO1-mediated IL-6 production also plays an important role in supporting the development of pro-tumorigenic MDSCs and disruption of IDO1 reduced IL-6 production, attenuated MDSC suppressive activity, delayed tumor growth and increased survival in a KRAS-induced lung cancer model (Smith, et al. (2012) Cancer Discov 2(8): 722-735). The connection between IDO1-dependent depletion of tryptophan and kynurenine-dependent activation of AHR provides a lynch pin explaining why tryptophan catabolism is intimately associated with immune escape, a critical checkpoint that restrains cancer progression.

The regulation of IDO1 expression in the tumor microenvironment is complex. IDO1 was the first IFN-γ-regulated gene discovered (Yoshida, et al. (1981) Proc Natl Acad Sci USA 78(1): 129-132). In fact, there is a strong correlation between IFN-γ and IDO1 expression across all cancer histologies (http://cancergenome.nih.gov/). Additionally, IDO1 expression is upregulated by type I interferons, TLR ligands, TNF, IL-1, CTLA-4, CD200, GITR, CD40 and TGF-β, all of which play important roles in the immune system, and cancer development, progression and response to therapy. High IDO1 activity as measured by IDO1 expression, tryptophan depletion and/or increase in kynurenine has been implicated in the poor prognoses, reduced survival rates and increased metastatic potential of a wide variety of tumor types. As such, increases in serum levels of kynurenine with a concomitant reduction in tryptophan are evidenced in breast, colorectal cancer, head and neck, lung and prostate cancers (Liu, et al. (2010) Blood 115(17): 3520-3530). In addition, IDO1 is chronically activated in cancer patients (Schrocksnadel, et al. (2006) Clin Chim Acta 364(1-2): 82-90), associated with extensive disease (Huang, et al. (2002) Br J Cancer 86(11): 1691-1696), poor outcome and/or resistance to standard chemotherapy in several cancers including melanoma (Weinlich, et al. (2007) Dermatology 214(1): 8-14), acute myeloid leukemia (Chamuleau, et al. (2008) Haematologica 93(12): 1894-1898; Corm, et al. (2009) Leuk Res 33(3): 490-494), breast and cervical cancer (Inaba, et al. (2010) Gynecol Oncol 117(3): 423-428; Yu, et al. (2011) Clin Dev Immunol 2011: 469135; Yu, et al. (2013) J Immunol 190(7): 3783-3797; Chen, et al. (2014) Breast Cancer Res 16(4): 410): Clin Cancer Res. 2007 Dec. 1; 13(23):6993-7002; Trott, et al. (2016). Oncotarget, 7(41), 66540-66557, colorectal cancer, renal cell carcinoma, cutaneous melanoma, diffuse large B-cell lymphoma, endometrial cancer, gastric cancer, glioma, hepatocellular carcinoma, Hodgkin's lymphoma, laryngeal squamous cell carcinoma, lung cancer, multiple myeloma, Non-Hodgkin's lymphoma, esophageal and oral squamous cell carcinoma, osteosarcoma, ovarian cancer, pancreas ductal carcinoma, T-cell leukemia and thyroid carcinoma. IFN-γ is a critical effector cytokine secreted from activated NK and T-cells. Negative regulatory circuits that are engaged to restrain T-cell activity either systemically (CTLA-4) or locally (PD-L1/L2) are currently approved for use as anti-cancer agents where they enhance T-cell-mediated tumor growth inhibition. Genetic knockouts of checkpoints such as CTLA-4, PD-1 or PD-L1 result in the marked enhancement of IFN-γ production (Latchman, et al. (2004) Proc Natl Acad Sci USA 101(29): 10691-10696; Pandiyan, et al. (2007) J Immunol 178(4): 2132-2140), which can engage the immunosuppressive IFN-γ-to-IDO1 axis. The inhibition of intrinsic IDO1 expression with 1-Methyl Tryptophan in a mouse melanoma model, significantly improved the efficacy of Ipilimumab, a CTLA-4 blocking antibody (Holmgaard, et al. (2013) J Exp Med 210(7): 1389-1402). This enhanced efficacy of Ipilimumab was associated with an increase in CD8 effector cells and a decrease in Tregs. These observations were extended to other antibodies targeting PD1, PD-L1 and GITR where the inhibition of IDO1 enhanced their anti-cancer activity. Mechanistically IDO1 was shown to impede the efficacy of these checkpoint inhibitors through the induction of Tregs with the subsequent recruitment of MDSCs creating an immunosuppressive environment at the tumor (Holmgaard, et al. (2015) Cell Rep 13(2): 412-424). Immunotherapeutic approaches to treat cancer such as IFN-γ itself, innate immune activators such as CpG-ODNs, anti-4-1BB (CD137), anti-OX40, anti-PD-1/PD-L1/PD-L2, anti-CTLA 4 all have the potential to activate IDO1 expression restraining their long-term efficacy in the clinic. Therefore, there may be significant therapeutic potential in combining IDO1 inhibitors with these agents. Specifically, combination of IDO1 inhibitors with anti-PD1 antibodies (pidilizumab, nivolumab, pembrolizumab), anti-PD-L1 antibodies (durvalumab, atezolizumab, avelumab), anti-CTLA-4 antibodies (ipilimumab), anti-OX40 antibodies (MEDI6469, KHK4083) and anti-4-1BB (CD137) antibodies (PF-05082566) have significant therapeutic potential in a wide range of tumor types.

Taken together, these data suggest that inhibitors of tryptophan depletion and the concomitant production of kynurenine such as IDO1 inhibitors may be useful as a single agent or in combination in a variety of cancer types in both treatment naïve as well as treatment resistant cancer patients. This utility has been demonstrated by known IDO1 inhibitors such as epacadostat (INCB024360) and NLG919. Epacadostat is known to bind to IDO1 and block the catabolism of tryptophan and the subsequent production of kynurenine both in vitro and in vivo. Additionally, epacadostat has demonstrated single agent efficacy in pre-clinical mouse models, CT26 and PAN02, an effect that is dependent upon the presence of T-cells. (Yue, et al. (2009) J Med Chem 52(23): 7364-7367; Koblish, et al. (2010) Mol Cancer Ther 9(2): 489-498; Liu, et al. (2010) Blood 115(17): 3520-3530; Jochems, et al. (2016) Oncotarget, Advance Publications). The pre-clinical efficacy of epacadostat has translated into human clinical trial outcomes (NCT01195311).

The results of the following assays demonstrate evidence that the compounds exemplified herein are useful as kynurenine production inhibitors such as IDO1 inhibitors and may be useful in treating cancer. Furthermore, the results of the following assays demonstrate that certain exemplified compounds bind to IDO1 and that all exemplified compounds inhibit the conversion of tryptophan to kynurenine in cancer cells both in vitro and in vivo.

Binding Assay for IDO1

The purpose of this assay is to demonstrate that certain exemplified compounds bind to IDO1 in vitro. Specifically, this assay assesses the ability of test compounds to compete with a tritiated spy molecule 1-(2,4-difluorophenyl)-3-[[1-(3,4,5-tritritiobenzoyl)indolin-5-yl]methyl]urea and allows for the calculation of the binding affinity, $IC_{50}$.

Competitive Binding of 1-(2,4-Difluorophenyl)-3-[[1-(3,4,5-tritritiobenzoyl)indolin-5-yl]methyl]urea to IDO1

Load 300 nM $His_6$-IDO1 (Proteros, SwissProtID P14902, Cat# PR-0278, batch 19/59, 98 mg/mL in 25 mM MES pH 6.5, 150 mM KCl, purity >95%) diluted in DPBS to each well of nickel coated plate (Sigma, Cat#55563) and incubate overnight at 4° C. Remove unbound proteins by washing plate with 300 μL DPBS four times in BIOTEK® Microplate Washer. Add 100 μL of blocking buffer (0.05% TWEEN® 20/DPBS) per well and incubate for one hour at room temperature to reduce nonspecific binding. While blocking the plate, prepare 50 nM 1-(2,4-difluorophenyl)-3-[[1-(3,4,5-tritritiobenzoyl)indolin-5-yl]methyl]urea (Biocair, Cat# TRQ41455) by diluting in DPBS, and serially dilute unlabeled stock solution 2.5-fold in DMSO to generate an eleven point dilution curve. Add 5 μL of serial diluted unlabeled compounds to 95 μL of 50 nM 1-(2,4-difluorophenyl)-3-[[1-(3,4,5-tritritiobenzoyl)indolin-5-yl]methyl] urea, add mixture to the wells in the plate, and incubated at room temperature for four hours with gentle shaking. To determine the maximum displacement of the tritiated-spy molecule (1-(2,4-difluorophenyl)-3-[[1-(3,4,5-tritritiobenzoyeindolin-5-yl]methyl]urea), add an excess amount of unlabeled 1-(2,4-difluorophenyl)-3-{[1-(phenylcarbonyl)-2,3-dihydro-1H-indol-5-yl]methyl}urea (ChemDiv, Cat# G714-0242)) 100 µM to 50 nM difluorophenyl)-3-[[1-(3,4,5-tritritiobenzoyeindolin-5-yl]methyl]urea and add to non-specific binding control wells in the plate. After four hour incubation, aspirate wells using a MultiMek96 and wash the plate quickly once with 300 µL ice-cold DPBS using a BIOTEK® Microplate washer. Add 100 µL of 100 mM imidazole in PBS pH 7.5 to each well and incubated for 10 minutes at room temperature to displace IDO1-ligand complex from the nickel-coated plate. Transfer displaced IDO1-ligand complex into a 96-well white clear bottom plate (Costar, Cat#3632) containing 200 µL of Microscint-20 (Perkin Elmer, Cat#6013621), per well using a MultiMek96. Quantitate total bound and nonspecific binding (NSB) of the 1-(2,4-difluorophenyl)-3-[[1-(3,4,5-tritritiobenzoyl)indolin-5-yl]methyl]urea ligand using a Trilux Microbeta Counter. Use total bound and NSB values to calculate the $IC_{50}$ for unlabeled compound using nonlinear regression analysis in GraphPad Prism. The results of this assay demonstrate that certain exemplified compounds bind to IDO1. For example, Examples 1A and 1B demonstrate $IC_{50}$ values less than 1.5 µM. Specifically, the $IC_{50}$ for Example 1A is 0.033 µM±0.0028 (n=2).

Kynurenine Production Assay (SKOV3)

The purpose of this assay is to evaluate the inhibition of the production of kynurenine, N-formyl-kynurenine and the depletion of tryptophan in IDO1 expressing cancer cells and assess whether compounds are overtly toxic to these cells. Exemplary compounds are tested for the inhibition of IDO1 activity in SKOV3 (ATCC, Cat# HTB-77), an ovarian cancer cell line that intrinsically expresses IDO1. Due to IDO1 expression, SKOV3 cells degrade tryptophan with the concomitant production of kynurenine and compounds are tested for their ability to inhibit the production of kynurenine, N-formyl-kynurenine and the depletion of tryptophan. Optionally, overt toxicity of compounds can be assessed by monitoring cell viability.

Synthesis of Internal Standards

Synthesis of N-Formyl L-Kynurenine-d4(2S)-2-amino-4-oxo-4-(2,3,4,5-tetradeuterio-6-formamidophenyl)butanoic acid

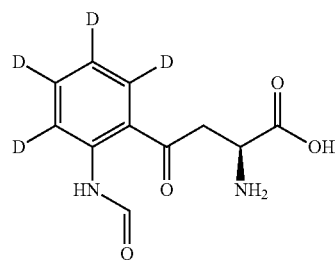 [SMILES: [2H]c1c([2H])c([2H])c(C(=O)C[C@H](N)C(=O)O)c(NC=O)c1[2H]]

Add a preformed mixture of acetic anhydride (0.026 mL, 0.264 mmol) in formic acid (0.052 mL, 1.32 mmol) to a mixture of L-kynurenine-d4 (56 mg, 0.264 mmol) in formic acid (0.132 mL). Stir the resulting mixture at room temperature under nitrogen for two hours. Dilute the reaction mixture with ACN and concentrate under a stream of nitrogen. Purify the residue by reversed-phase HPLC (Column: PHENOMENEX® LUNA® 5 µm C18 (2) 100 Å AXIA, 30×75 mm; eluent: A: 0.1% formic acid/water, B: 0.1% formic acid/ACN; gradient: 0% B for 2 minutes then gradient to 22% B over 5 minutes; flow: 85 mL/minutes at UVW 231/214 nm) to give the title compound 29 mg as a fluffy white solid after lyophilization. ES/MS (m/z): 241.0 (M+H).

Cell Treatment and Cell Viability

Plate SKOV3 cells, an IDO1-expressing ovarian cancer cell line, at 20,000 cells per well in 100 µL of McCoys 5A media (Gibco, Cat#16600-082) supplemented with non-essential amino acids (Gibco, Cat#11140-050), 1 mM sodium pyruvate (Gibco, Cat#11360-070), and 10% fetal bovine serum, complete media, in a 96 well tissue culture plate (BD Biosciences). Then, incubate cells for 16 hours in a 37° C. incubator with 5% $CO_2$. Prepare compound serial dilutions from 10 mM stock test compounds in DMSO. Serially dilute the stock solution 3-fold in DMSO, and transfer 5 µL of compounds to an intermediate dosing plate containing 95 µL of complete media to generate a ten-point dilution curve with final compound concentrations ranging from either 1 µM to 0.5 pM or 10 µM to 0.5 nM. Decant the media from the plate containing cells and blot onto paper towels. Wash plate twice with 90 µL of complete media per well and replace the final wash with 90 µL of complete media. After washing, add 10 µL of serial diluted compounds from the intermediate dosing plate to each well of the plate(s) and incubate for 18 hours in a 37° C. incubator with 5% $CO_2$. The final DMSO concentration in the assay is 0.5%. At the end of the 18 hours incubation, transfer 50 µL of media from each well into a 96 well v-bottom plate (Thermo Scientific), seal the plate, and store at −80° C. for subsequent mass spectrometric-based measurement of kynurenine, N-formyl-kynurenine and tryptophan. Optionally, return original plate(s) to the incubator for an additional 24 hours and measure the viability of cells by adding an equal volume of CELLTITER-GLO® (Promega) and measure luminescence in an PERKIN ELMER® EnVision plate reader.

Mass Spectrometric (MS) Measurement of Tryptophan, N-Formyl-kynurenine, and Kynurenine Thaw samples collected from SKOV3 cell-based assay on ice and clear any cellular debris by centrifuging plate at 3220×g for one minute at 4° C. Add 12.5 µL of internal standards consisting of 2.5 µg/mL L-tryptophan-2',4',5',6',7'-d5 (CDN Isotopes, Cat# D-1522), L-kynurenine sulfate-ring-d4,3,3-d2 (Cambridge Isotope Laboratories, Cat# DLM-7842-0.01) and internally prepared N-formyl L-kynurenine-d4. Heat seal all plates with Easy Peel seals (ThermoScientific) and mix by vortexing for 1-2 minutes and then centrifuge for one minute at 3220×g at 4° C. Generate standard calibration solutions for quantification of kynurenine and N-formylkynurenine by dissolving each in water to give a final concentration of 1 mg/mL. Aliquot 20.8 µL kynurenine and 23.6 µL N-formylkynurenine from their respective 1 mg/mL stock and dilute to 1 mL using McCoys 5A media to give a final concentration for each standard of 100 µM. Serial dilute calibration solution 2-fold in complete media to obtain a 5-point standard curve with final concentrations of 5 µM to 0.313 µM (kynurenine) and 2 µM to 0.125 µM (N-formylkynurenine). Inject 1 µL of media sample (unknown) or standard calibration solution onto an LC/MS-MS system consisting of a SHIMADZU® Prominence 30A HPLC system and an AB SCIEX® 5500 triple quadrupole mass spectrometer. Separate analytes on a XBridge™ C18 column, 2.1×50 mm, 3.5 µm (Waters, Cat#186003021) maintained at 35° C., with mobile phase flow rate of 0.7 mL/minute. The mobile phase A is 0.1% formic acid in water, and mobile phase B is MeOH. The gradient profile is: 0 minutes, 0.5% B; 0.8 minutes, 98% B; 1.10 minutes, 98% B; 1.11 minutes, 0.5% B; 1.7 minutes, and then stopped. Operate the mass spectrometer in APCI positive multiple reaction monitoring mode. Use data from standard curve samples and generate a linear fit calibration curve for each analyte using the MultiQuan™ software. Use the standard curve generated to calculate the analyte concentrations for the unknowns.

Calculate compound $IC_{50}$ values using the mass spectrometric measurement of kynurenine from the media containing 500 µM of reference standard treatment as one hundred percent inhibition, and no compound but DMSO treatment as zero percent inhibition. Measurements of N-formyl-kynurenine and tryptophan are used to assess the validity of data generated by showing direct relationship between kynurenine and N-formyl-kynurenine production with the concomitant reduction in tryptophan levels. The results of this assay demonstrate that all exemplified compounds inhibit the production of kynurenine and N-formyl-kynurenine in IDO1 expressing cancer cells at $IC_{50}$ values for inhibiting both kynurenine and N-formyl-kynurenine of less than 0.9 µM and of those tested (Examples 1-9) in cell viability, all of the compounds did so without being overtly toxic to the cells up to at least 1 µM. For example, the $IC_{50}$ for Example 1A for inhibiting kynurenine and N-formyl-kynurenine are 0.007 µM±0.002 (n=6) and 0.007 µM±0.002 (n=6) respectively. Furthermore, Example 1A does not inhibit cell proliferation up to 10 µM.

In Vivo Target Inhibition Assay

The purpose of this assay is to evaluate the inhibition of kynurenine production and tryptophan depletion in cancer cells in vivo. SKOV3X (Indiana University Research and Technology Center), an ovarian cancer cell line, intrinsically expresses IDO1 and readily forms tumors in the peritoneal cavity of Athymic Nude-Foxn1$^{nu}$ mice (Harlan). As a consequence of IDO1 expression, SKOV3X tumors locally deplete tryptophan with the concomitant production of high levels of kynurenine in the tumor microenvironment. The purpose of this assay is to measure the ability of test compounds to inhibit IDO1 evidenced by the clear reduction in kynurenine levels in the tumor.

Live Phase

Culture SKOV3X in McCoys 5A media (Gibco, Cat#16600-082) supplemented with non-essential amino acids (Gibco, Cat#11140-050), 1 mM sodium pyruvate (Gibco, Cat#11360-070) and 10% FBS and incubate at 37° C. in 5% $CO_2$. Trypsinize and isolate cells from culture and resuspend cells in Hank's balanced salt solution (HBSS). Implant $2×10^6$ SKOV3X cells into the intraperitoneal cavity of each Athymic Nude-Foxn1$^{nu}$ mouse (Harlan). Approximately three weeks post-implantation, palpate animals to ensure tumor formation and randomize tumor-bearing mice into vehicle control and compound treatment groups. Administer compound formulated in vehicle containing 1% hydroxyethylcellulose (HEC) and 0.025% TWEEN® 80 and 0.05% Antifoam or vehicle alone by oral gavage. Generate time-course inhibition profile by dosing tumor-bearing animals with a single dose and collect plasma, liver, and tumor samples at 2, 4, 8, 12, and 24 hours post dose. Collect blood into EDTA-containing blood collection tubes (Greiner bio-one, Cat#450474) and centrifuge at 2365×g, isolate plasma, and freeze at −80° C. Isolate liver and tumor fragments, record weights and flash freeze and store at −80° C.

Generation of Standard Curve, Tissue Processing and Target Inhibition

Prepare calibration standards for L-kynurenine and L-tryptophan by first generating stripped matrices, which are plasma and tissue homogenates depleted of L-kynurenine and L-tryptophan by dialysis. Then, fortify stripped matrices with known amounts of L-kynurenine and L-tryptophan. Generate stripped mouse plasma by adding 10 mL of EDTA treated mouse plasma (BioreclamationIVT, Cat# MSEPLEDTA3) to a SPECTRA/POR® FLOAT-A-LYZER® G2 (Spectrum Labs, Cat# G235063) and placing this dialysis device in 1000 mL of phosphate buffered saline and dialyze overnight. Afterward, transfer this device to a fresh 1000 mL of phosphate buffered saline and repeat the dialysis. Transfer the stripped mouse plasma to a clean container and store at −20° C. for future use. Prepare control liver homogenate by adding 3 mL of MeOH/water (1:1, v/v) for every gram of control mouse liver and homogenize with an ultrasonic probe. Prepare control tumor homogenate in the same fashion except use a tissue grinder to homogenize tumor tissue. Add 10 mL of the control tissue homogenates, liver and tumor, to separate SPECTRA/POR® FLOAT-A-LYZER® G2 devices and dialyze each overnight in 1000 mL of MeOH/water (1:1, v/v), then transfer each to a fresh 1000 mL of MeOH/water (1:1, v/v) and repeat the dialysis. Transfer the stripped tissue homogenates to separate containers and store at −20° C. for future use.

Prepare standard stock solutions of L-kynurenine-sulfate (Sigma Aldrich, Cat# K3750), dissolved in ACN/water (1:1, v/v) and L-tryptophan (Sigma Aldrich), dissolved in N-methyl-2-pyrrolidone/water (4:1, v/v), to give final free base concentrations of 1 mg/mL. Aliquot 50 µL of the respective stock solutions and dilute with MeOH/water (1:1, v/v) to yield a combined 50 µg/mL working solution. Prepare six additional calibration working solutions in MeOH/water (1:1, v/v) by serial dilution of the 50,000 ng/mL solution to obtain a 7-point calibration curve with final concentrations of 25 ng/mL to 50 µg/mL.

Mix liver samples acquired from test subjects with MeOH/water (1:1, v/v) in a proportion of 1 gram of tissue to 3 mL of solvent and homogenized with an ultrasonic probe. Homogenize tumor samples with the same proportion of MeOH/water (1:1, v/v) using a tissue grinder. Thaw plasma samples from test subjects and mix for homogeneity.

Perform extraction of calibration working solutions, the 7-point dilution series of L-kynurenine and L-tryptophan, by transferring 25 µL of each sample to separate wells of a 96-well plate and add 25 µL of the appropriate stripped control matrix (plasma, liver or tumor homogenate) to these wells depending upon tissue of origin of test samples. Add 25 µL of MeOH/water (1:1, v/v) to separate wells followed by 25 µL of the respective test samples. Next, add 180 µL of ACN/MeOH (1:1, v/v) containing 250 ng/mL of L-tryptophan-2',4',5',6',7'-d5 (Sigma Aldrich, Cat#615862) and L-kynurenine sulfate-ring-d4,3,3-d2 (Cambridge Isotope Laboratories, Cat# DLM-7842-0.005) to all wells and mix to precipitate proteins in the samples. Centrifuge the 96-well plate to pellet the precipitated protein material then dilute a portion of each supernatant at least 10-fold with water/TFA (100:2, v/v). Inject 10 µL of each extracted sample and calibration standard onto an LC/MS-MS system consisting of a SHIMADZU® SCL-10A controller with SHIMADZU® LC-10ADvp HPLC pumps, a CTC-PAL autosampler and an AB SCIEX® 4000 triple quadrupole mass spectrometer. Separate the analytes on an Advantage™ Echelon™ C18 column, 2.1×20 mm, 4 µm (Analytical Sales and Service, Cat# Sprite AE1822) maintained at ambient conditions with a mobile phase flow rate of 1.5 mL/minute. Mobile phase A is water/TFA/1 M ammonium bicarbonate, (1000:4:1, v/v/v) and mobile phase B is ACN/TFA/1 M ammonium bicarbonate 1000:4:1, v/v/v). The gradient profile is: 0 minutes, 0.3% B; 0.03 to 0.2 minutes, 7% B; 0.3 to 0.4 minutes, 36% B; 0.41 minutes, 98% B, then stopped at 0.7 minutes to return to the original conditions. Operate the mass spectrometer in TURBOIONSPRAY® positive multiple reaction monitoring mode. Use data from calibration standards curve samples and generate a quadratic fit calibration curve for each analyte using the Analyst™ software. Use the standard curve generated to calculate the analyte concentrations for the study samples.

Use the liver concentration of kynurenine from non-tumor-bearing animals treated with vehicle as maximum inhibition or lowest level of kynurenine. Use the SKOV3X tumor concentration of kynurenine from vehicle-treated tumor-bearing mice as minimum inhibition or highest level of kynurenine. Calculate the percent inhibition for compound treated groups relative to the minimum IDO1 inhibition in the vehicle-treated tumor. The results of this assay demonstrate that Example 1A inhibits the production of kynurenine and N-formyl-kynurenine in IDO1 expressing cancer cells in vivo. Specifically, Example 1A dosed at 75 mg/kg, 25 mg/kg and 5 mg/kg resulted in 79%, 59% and 37% inhibition respectively 12 hours after dosing.

Anti-Tumor Effect of Example 1A in Mouse Syngeneic Colon26 Model for Colon Cancer and in Combination with LY3300054 in Established L55 Humanized Mouse Model Mouse Syngeneic Colon 26 Model:

Grow the mouse BALB/c-derived Colon26 colon cancer cell line in RPMI 1640 medium supplemented with 10 mM HEPES, 1 nM sodium pyruvate, and 10% fetal bovine serum. Harvest sub-confluent cells with trypsin and rinse twice with complete growth medium lacking serum. Initiate subcutaneous tumors by injecting $1×10^6$ cells resuspended in HBSS in the rear flank of immune-competent BALB/c mice (Envigo, Indianapolis, Ind.). Six days after tumor implantation, randomize animals based on body weight and place into their respective treatment groups using the number of animals per group as indicated.

L55 Humanized Tumor Model, hPBMC Challenge, and Treatment:

Grow the human NSCLC cell line, L55, in RPMI 1640 medium supplemented with 10% fetal bovine serum. Harvest sub-confluent cells with trypsin and rinse twice with growth medium lacking serum. Initiate the growth of subcutaneous tumors by injecting $5×10^6$ in a 1:1 mixture of HBSS and MATRIGEL® (BD Biosciences, Franklin Lakes, N.J.) in the rear flank of NOD.Cg-Prkdc$^{scid}$Il2rg$^{tm1Wjl}$/SzJ mice more commonly known as NOD scid gamma chain knockout mice (NSG) mice (The Jackson Laboratory, Bar Harbour, Me.), which lack T cells, B cells, NK cells, and are deficient in cytokine signaling. When the mean tumor volume reaches approximately 200-300 mm$^3$, randomize the animals by tumor size and body weight and place into their respective treatment groups as indicated. After randomization, challenge tumor-bearing mice with PBS alone (no PBMCs) or with PBS containing $1×10^7$ human PBMCs into the tail vein of recipients.

Data Capture, Compound Formulation and Vehicle Controls (Both Models)

Capture tumor size and body weight using Study Director. Estimate tumor volume (V) by using the formula: V=0.536× L×W$^2$ where L=larger measured diameter and W=smaller of the perpendicular diameter. Transform the tumor volume data to a log scale to equalize variance across time and treatment groups. Analyze the log volume data with a two-way repeated measures analysis of variance by time and treatment using the MIXED procedures in SAS software (Version 9.2). The correlation model for the repeated measures is Spatial Power. Compare treated groups to the control group at each time point. Use the MIXED procedure also separately for each treatment group to calculate adjusted means and standard errors at each time point. Both analyses account for the autocorrelation within each animal and for the loss of data that occurs when animals with large tumors are removed from the study early. Calculate relative changes in tumor volume (% T/C) using the tumor volume measurements taken nearest to the last day of dosing with Example 1A, using the formula % T/C=100×ΔT/ΔC, where T=mean tumor volume of the compound treated group, ΔT=mean tumor volume of the compound treated group minus the mean tumor volume on the baseline day, C=mean tumor volume of the control (vehicle) group, and ΔC=mean tumor volume of the control group minus the mean tumor volume on the baseline day. If ΔT<0, then a tumor regression value is calculated instead of % T/C whereby % Regression=100× ΔT/T$_{initial}$ such that T$_{initial}$=mean tumor volume on the baseline day.

Assess antitumor efficacy of Example 1A and LY3300054 alone, or in combination by measuring tumor volume by three dimensional caliper measurements twice a week during the course of the study. Measure body weight twice weekly during the course of the study, as a general indicator of tolerability.

Formulations for Example 1A and LY3300054: Formulate Example 1A on a weekly basis in 1% HEC/0.25% Tween 80/0.05% Antifoam and store at 4° C. Solublize LY3300054 in phosphate buffered saline and store at 4° C.

Control group(s): For single agent efficacy studies, administer vehicle for Example 1A alone. For combination studies, administer both vehicles used for Example 1A and LY3300054 according to the same schedule for each compound, respectively. For monotherapy groups in combination efficacy studies, treat the animals with the desired compound and the vehicle for the compound not being dosed following the schedule for the non-dosed compound.

Colon26 Syngeneic Model, Treatment and Results:

MONOTHERAPY EXAMPLE 1A

Treat female BALB/c mice (n=10) bearing Colon26 tumors with Example 1A twice daily for 21 days by oral gavage at doses of 10, 50, and 100 mg/kg. Start administration of Example 1A six days after tumor implantation, and monitor tumor growth and body weight twice a week for the duration of the treatment period.

Results:

Treatment with 10, 50, and 100 mg/kg of Example 1A resulted in a dose-responsive effect on tumor growth with only 50 and 100 mg/kg doses showing statistically (p<0.001) relevant growth inhibition at day 20. The changes in tumor volume (% T/C) observed at day 20 were 17.5%, 31.2%, and 62.6% for the 10, 50, and 100 mg/kg doses, respectively. There were no significant tolerability issues at any dose tested with Example 1A with respect to body weight changes over the course of treatment compared to a vehicle-treated mice. Body weight loss was measured as the percent change from mean body weights recorded on baseline 6 days after tumor implant for each group. At day 20, the average vehicle treated mice showed 5.5% reduction in body weight compared to baseline with the 10, 50, and 100 mg/kg dosed groups showing a 2.5%, 8%, and 2.5% reduction, respectively. While there was a dose-dependent trend in body weight loss with regard to dose, they were not statistically different from vehicle-treated mice.

L55 Humanized Tumor Model, Treatment and Results:
hPBMC Effect on L55 Tumor Growth The L55 NCLC human cancer cell line is intrinsically resistant to the allo-response associated with the injection of hPBMCs. The goal of these studies is to assess the ability of compounds to potentiate the allo response allowing human T cells to target and restrict the growth of a human L55 tumors in a mouse that lacks an adaptive immune system (NSG mice). To assess the contribution of hPBMCs on tumor growth inhibition of the L55 tumors, mock inject NSG mice bearing established L55 tumors (n=10) that have reached approximately 250 mm$^3$ with PBS lacking hPBMCs, or PBS containing 1×10$^7$ hPBMCs. Measure tumor volume and body weight twice a week for the duration of the treatment period.

Results:

There was no statistically significant inhibition of L55 tumor growth when compared to animals that did not receive hPBMCs over the course of the study. No significant tolerability issues were observed with the injection of human PBMCs over the course of the study evidenced by the lack of significant weight loss when compared to baseline, which at day 41 was 0.1% lower than at baseline.

MONOTHERAPY EXAMPLE 1A

To assess the ability of Example 1A to enhance L55 tumor growth inhibition mediated by hPBMCs, mock inject NSG mice bearing established L55 tumors (n=10) that have reached approximately 250 mm$^3$ with PBS lacking hPBMCs, and and another group (n=10) with PBS containing 1×10$^7$ hPBMCs. Treat both groups with 75 mg/kg Example 1A by oral gavage twice daily for 21 days. Measure tumor volume and body weight twice a week for the duration of the treatment period.

Results:

In the absence of hPBMCs, treatment of L55 tumors with Example 1A did not result in significant tumor growth inhibition over the course of the treatment when compared to vehicle alone without PBMCs. Treatment of L55 tumor-bearing animals with Example 1A in the presence of hPBMCs resulted in tumor growth inhibition when compared to the vehicle control group lacking hPBMCs. Statistically relevant suppression of tumor growth was most apparent at later time points with a % T/C of 47.6% at day 41 (P<0.001). No significant tolerability issues were apparent over the course of the study with hPBMCs, Example 1A, or the combination evidenced by the lack of statistically significant reductions in body weight loss when compared to baseline measurements.

Monotherapy LY3300054

To assess the ability of LY3300054 to enhance L55 tumor growth inhibition mediated by hPBMCs, inject two groups of NSG mice bearing established L55 tumors (n=10/group) that have reached approximately 250 mm$^3$ with PBS containing hPBMCs. Treat one group with 10 mg/kg IgG-effector null (IgG-EN) control antibody and the other with 10 mg/kg LY3300054 by intraperitoneal injection once a week for 4 weeks. Measure tumor volume and body weight twice a week for the duration of the treatment period.

Results:

Treatment of L55 tumor-bearing mice that were injected with hPBMCs with 10 mg/kg IgG-EN did not alter tumor growth or progression when compared to vehicle alone with or without hPBMCs. Treatment of L55 tumor-bearing animals that had been injected with hPBMCs with 10 mg/kg LY3300064 resulted in statistically significant tumor growth inhibition when compared to vehicle-treated controls that contained or lacked hPBMCs. The change in tumor volume (% T/C) observed at the end of the dosing period when compared to vehicle alone lacking PBMCs (day 37) was 75.7%. No significant tolerability issues were apparent over the course of the study with LY3300054 with or without hPBMCs evidenced by the lack of statistically significant reductions in body weight loss when compared to baseline measurements.

COMBINATION OF EXAMPLE 1A AND LY3300054

Inject NSG mice (n=10) bearing L55 tumors that have reached approximately 250 mm$^3$ with hPBMCs and treat with 75 mg/kg Example 1A twice a day by oral gavage for 21 days and 10 mg/kg LY3300054 by intraperitoneal injection once a week for 4 weeks. Measure tumor volume and body weight twice a week for the duration of the treatment period.

Results:

Combined treatment of 75 mg/kg Example 1A and 10 mg/kg LY3300054 resulted in an improvement in the anti-tumor efficacy when compared to either monotherapy group alone. Tumor volumes were significantly lower than the vehicle alone groups that either lacked PBMCs or were injected with hPBMCs (P<0.001 at all measurements). Tumor volumes on days 30, 34, 37, and 41 were 9.6% T/C, 19.8% T/C, 13.3% T/C, and 27.3% T/C, respectively. The difference in the anti-tumor efficacy between monotherapy groups compared to the combination group was statistically significant (p<0.001). To assess whether or not the combination was additive or synergistic, the data is analyzed essentially as follows:

Statistical Analysis (Both Models):

The statistical analysis of the tumor volume data begins with a data transformation to a log scale to equalize variance across time and treatment groups. The log volume data are analyzed with a two-way repeated measures analysis of variance by time and treatment using the MIXED procedures in SAS software (Version 9.3). The correlation model for the repeated measures is Spatial Power. Treated groups are compared to the control group at each time point. The MIXED procedure is also used separately for each treatment group to calculate adjusted means and standard errors at each time point. Both analyses account for the autocorrelation within each animal and the loss of data that occurs when animals with large tumors are removed from the study early. The adjusted means and standard errors (s.e.) are plotted for each treatment group versus time.

Combination Analysis Method (Bliss Independence for IVEF Studies):

With the results of the repeated measures analysis, contrast statements are used to test for an interaction effect at each time point, comparing the mean of the vehicle and combination groups to the mean of the two single agent groups. This is equivalent to the Bliss Independence method for testing additivity. The expected additive response (EAR) for the combination is calculated on the tumor volume scale as: EAR volume=V1*V2/V0, where V0, V1, and V2 are the estimated mean tumor volumes for the vehicle control, treatment 1 alone, and treatment 2 alone, respectively. If the interaction test is significant, the combination effect is declared statistically more than additive or less than additive depending on the observed combination mean volume being less than or more than the EAR volume, respectively. Otherwise, the statistical conclusion is additive.

Using this method of analysis, the tumor growth inhibition was not better than additive until days 34 and 37 where tumor growth inhibition was synergistic with P<0.008 and p<0.001, respectively. No significant tolerability issues were apparent over the course of the study with the combination of Example 1A and LY3300054 evidenced by the lack of statistically significant reductions in body weight loss when compared to baseline measurements.

The compounds of the present invention are preferably formulated as pharmaceutical compositions administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (D. Troy, et al., eds., 21st ed., Lippincott Williams & Wilkins, 2005).

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the daily range of about 0.05-1000 mg. Preferably such doses fall within the daily range of 0.1-500 mg. More preferably such doses fall within the daily range of 1-200 mg. In some instances dosage levels below the lower limit of the aforesaid ranges may be more than adequate, while in other cases still larger doses may be employed without causing any harmful side effect, and therefore the above dosage ranges are not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of the formula:

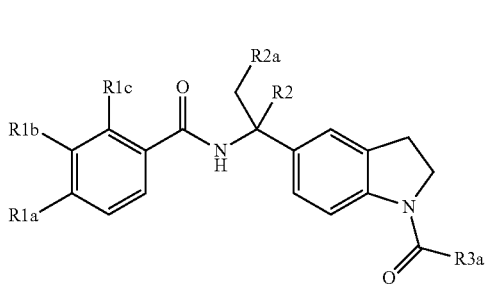

wherein:

R1a is hydrogen, methyl, ethenyl, cyano, fluoro, chloro, fluoromethyl, or difluoromethyl;

R1b is hydrogen, fluoro, or chloro;

R1c is hydrogen, hydroxy, fluoro, benzyloxy, or hydroxyethylamino;

R2 is hydrogen or methyl;

R2a is hydrogen or methyl; and

R3a is tetrahydropyranyl.

2. The compound according to claim 1 which is:

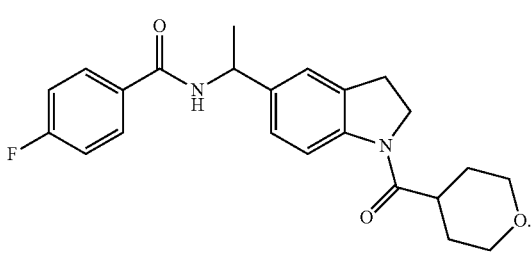 [SMILES: CC(NC(=O)c1ccc(F)cc1)c1ccc2c(c1)CCN2C(=O)C1CCOCC1]

3. The compound according to claim 2 which is:

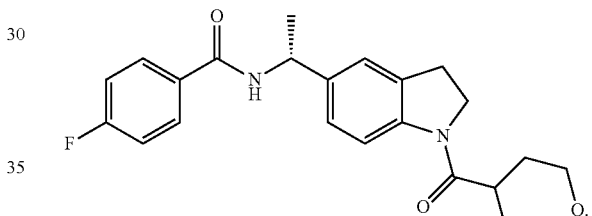

4. The compound according to claim 2 which is:

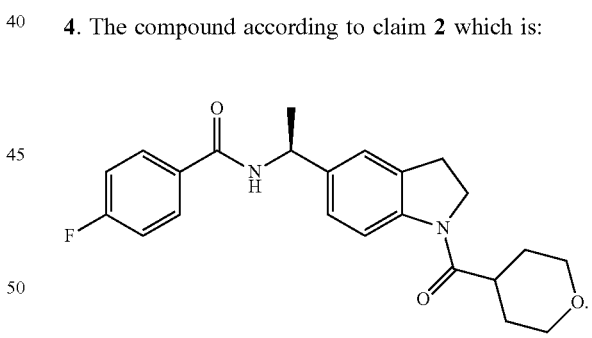

5. The compound according to claim 3 which is crystalline 4-fluoro-N-{(1R)-1-[1-(tetrahydro-2H-pyran-4-ylcarbonyl)-2,3-dihydro-1H-indol-5-yl]ethyl}benzamide.

6. The compound according to claim 5 which is crystalline 4-fluoro-N-{(1R)-1-[1-(tetrahydro-2H-pyran-4-ylcarbonyl)-2,3-dihydro-1H-indol-5-yl]ethyl}benzamide characterized by an X-ray powder diffraction pattern (Cu radiation, λ-1.54060 Å) comprising at least one peak at 17.38° in combination with one or more peaks selected from the group consisting of 12.51°, 15.65°, 16.37°, 17.56°, 21.48° and 25.23° (2θ±0.2°).

7. A pharmaceutical composition comprising a compound of the formula:

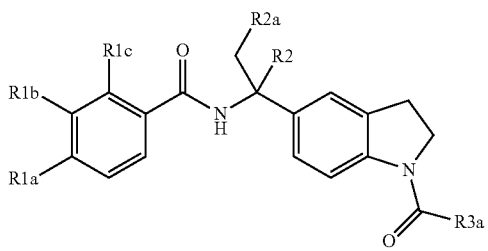

wherein:
R1a is hydrogen, methyl, ethenyl, cyano, fluoro, chloro, fluoromethyl, or difluoromethyl;
R1b is hydrogen, fluoro, or chloro;
R1c is hydrogen, hydroxy, fluoro, benzyloxy, or hydroxyethylamino;
R2 is hydrogen or methyl;
R2a is hydrogen or methyl; and
R3a is tetrahydropyranyl; with one or more pharmaceutically acceptable excipients, carriers or diluents.

8. A method of treating a patient with a cancer selected from the group consisting of melanoma, acute myeloid leukemia, chronic lymphocytic leukemia, colorectal cancer, renal cell carcinoma, breast cancer, lung cancer, ovarian cancer, fallopian tube carcinoma, primary peritoneal carcinoma, cervical cancer, gastric cancer, liver cancer, pancreatic cancer, thyroid cancer, glioma, non-Hodgkin's lymphoma, and Hodgkin's lymphoma comprising administering to the patient an effective amount of a compound of the formula:

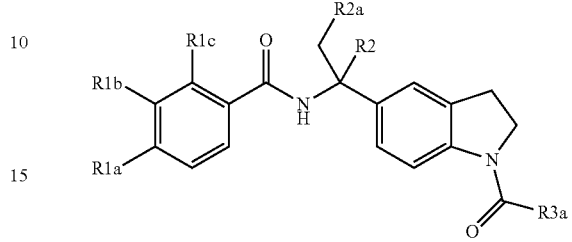

wherein:
R1a is hydrogen, methyl, ethenyl, cyano, fluoro, chloro, fluoromethyl, or difluoromethyl;
R1b is hydrogen, fluoro, or chloro;
R1c is hydrogen, hydroxy, fluoro, benzyloxy, or hydroxyethylamino;
R2 is hydrogen or methyl;
R2a is hydrogen or methyl; and
R3a is tetrahydropyranyl.

* * * * *

UNITED STATES PATENT AND TRADEMARK OFFICE
CERTIFICATE OF CORRECTION

PATENT NO. : 9,872,853 B2
APPLICATION NO. : 15/609115
DATED : January 23, 2018
INVENTOR(S) : Jolie Anne Bastian et al.

Page 1 of 1

It is certified that error appears in the above-identified patent and that said Letters Patent is hereby corrected as shown below:

On the Title Page

Column 2, Other Publications, Line 12, please delete "(ID01)" and insert --(IDO1--, therefor.

Signed and Sealed this
Tenth Day of April, 2018

Andrei Iancu
*Director of the United States Patent and Trademark Office*

SEQUENCE LISTING

```
<160> NUMBER OF SEQ ID NOS: 13

<210> SEQ ID NO 1
<211> LENGTH: 290
<212> TYPE: PRT
<213> ORGANISM: Artificial Sequence
<220> FEATURE:
<223> OTHER INFORMATION: Synthetic construct

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110
```

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Lys Ala Ser Gly Gly Thr Phe Ser Ser Tyr Ala Ile Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 16
<212> TYPE: PRT
<213> ORGANISM: Artificial Sequence
<220> FEATURE:
<223> OTHER INFORMATION: Synthetic construct

<400> SEQUENCE: 4

Ala Arg Ser Pro Asp Tyr Ser Pro Tyr Tyr Tyr Gly Met Asp Val
1               5                   10                  15

```
<210> SEQ ID NO 5
<211> LENGTH: 13
<212> TYPE: PRT
<213> ORGANISM: Artificial Sequence
<220> FEATURE:
<223> OTHER INFORMATION: Synthetic construct

<400> SEQUENCE: 5

Ser Gly Ser Ser Ser Asn Ile Gly Ser Asn Thr Val Asn
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Tyr Gly Asn Ser Asn Arg Pro Ser
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic construct

<400> SEQUENCE: 7

Gln Ser Tyr Asp Ser Ser Leu Ser Gly Ser Val
1               5                   10

<210> SEQ ID NO 8
<211> LENGTH: 123
<212> TYPE: PRT
<213> ORGANISM: Artificial Sequence
<220> FEATURE:
<223> OTHER INFORMATION: Synthetic construct

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser
        115                 120

<210> SEQ ID NO 9
<211> LENGTH: 111
<212> TYPE: PRT
<213> ORGANISM: Artificial Sequence
<220> FEATURE:
<223> OTHER INFORMATION: Synthetic construct
```

<400> SEQUENCE: 9

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly
            100                 105                 110
```

<210> SEQ ID NO 10
<211> LENGTH: 453
<212> TYPE: PRT
<213> ORGANISM: Artificial Sequence
<220> FEATURE:
<223> OTHER INFORMATION: Synthetic construct

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240
```

```
Glu Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 11
<211> LENGTH: 216
<212> TYPE: PRT
<213> ORGANISM: Artificial Sequence
<220> FEATURE:
<223> OTHER INFORMATION: Synthetic construct

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

```
Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 12
<211> LENGTH: 1359
<212> TYPE: DNA
<213> ORGANISM: Artificial Sequence
<220> FEATURE:
<223> OTHER INFORMATION: Synthetic construct

<400> SEQUENCE: 12
caggtccagc tggtccagtc aggggccgag gtcaaaaagc cagggtcatc tgtcaaagtg      60
tcttgtaagg catccggggg cacatttttcc agctacgcta tctcctgggt gagacaggca    120
ccagggcagg gtctggagtg gatgggcgga atcattccca tcttcgggac cgccaactac    180
gctcagaagt tcagggaag gtcactatt accgccgaca aaagcacatc tactgcttat     240
atggagctgt ctagtctgag gtctgaagat accgcagtgt actattgcgc ccggagtccc    300
gactatagcc cttactatta ctatggcatg gatgtctggg gccagggaac cacagtgaca    360
gtctcatccg ctagcaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca aatcttgtga caaaactcac acatgcccac cgtgcccagc acctgaagcc    720
gagggggcac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt atgtggacgg cgtggaggtg cataatgcca agacaaagcc gcgggaggag    900
cagtacaaca gcacgtaccg tgtggtcagc gtcctcaccg tcctgcacca agactggctg    960
aatggcaagg agtacaagtg caaggtctcc aacaaagccc tcccatcctc catcgagaaa   1020
accatctcca aagccaaagg gcagccccga gaaccacagg tgtacaccct gcccccatcc   1080
cgggaggaga tgaccaagaa ccaagtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctatt ccaagctcac cgtggacaag   1260
agcaggtggc agcaggggaa cgtcttctca tgctccgtga tgcatgaggc tctgcacaac   1320
cactacacgc agaagagcct ctccctgtct ccgggcaaa                           1359

<210> SEQ ID NO 13
<211> LENGTH: 648
<212> TYPE: DNA
<213> ORGANISM: Artificial Sequence
```

```
<220> FEATURE:
<223> OTHER INFORMATION: Synthetic construct

<400> SEQUENCE: 13
cagtccgtcc tgacacagcc accctcagcc tctggcaccc ctgggcagcg agtgacaatc      60
tcttgttctg ggagttcctc aaatattggt agtaacaccg tgaattggta ccagcagctg     120
cccggcacag cacctaagct gctgatctat ggaaactcaa ataggccatc cggagtcccc     180
gaccggttct ctggtagtaa atcaggcact tccgccagcc tggctattag cgggctgcag     240
tctgaggacg aagccgatta ctattgccag tcttacgatt ccagcctgtc tggaagtgtg     300
tttggcggag ggatcaagct gaccgtcctg ggccagccta aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540
tacctgagcc tgacgcctga gcagtggaag tcccacagaa gctacagctg ccaggtcacg     600
catgaaggga gcaccgtgga aagacagtg gcccctgcag aatgctct                   648
```